United States Patent [19]

Wurtman

[11] Patent Number: 5,449,683
[45] Date of Patent: Sep. 12, 1995

[54] METHODS OF INDUCING SLEEP USING MELATONIN

[75] Inventor: Richard J. Wurtman, Boston, Mass.

[73] Assignee: Massachussetts Institute of Technology, Cambridge, Mass.

[21] Appl. No.: 93,317

[22] Filed: Jul. 16, 1993

Related U.S. Application Data

[63] Continuation-in-part of Ser. No. 955,304, Oct. 1, 1992, abandoned.

[51] Int. Cl.⁶ ............................................. A61K 31/405
[52] U.S. Cl. ..................................... 514/415; 514/923
[58] Field of Search ....................... 514/923, 415, 416; 548/491

[56] References Cited

U.S. PATENT DOCUMENTS

| | | | |
|---|---|---|---|
| 4,600,723 | 7/1986 | Short et al. | 514/416 |
| 4,665,086 | 5/1987 | Short et al. | 514/416 |
| 4,687,763 | 8/1987 | Wurtman | 514/53 |
| 5,242,941 | 9/1993 | Lewy et al. | 514/416 |
| 5,362,745 | 11/1994 | Graziella | 514/415 |

FOREIGN PATENT DOCUMENTS

| | | |
|---|---|---|
| 0513702A2 | 11/1992 | European Pat. Off. . |
| 0578620A1 | 1/1994 | European Pat. Off. . |
| 55057563 | 4/1980 | Japan . |
| 4018034 | 1/1992 | Japan . |
| WO93/07870 | 4/1993 | WIPO . |

OTHER PUBLICATIONS

Dawson, D. et al, "Melatonin and Sleep in Humans," *J. Pineal. Res.*, 15:1–12 (1993).

Lewy, A. J., et al., "The Use of Plasma Melatonin Levels and Light in the Assessment and Treatment of Chronobiologic Sleep and Mood Disorders," *J. Neural. Transm.*, 21:311–322 (1986).

Borbély, A. A., "Endogenous Sleep–Substances and Sleep Regulation,"0 *J. Neural Transm.*, 21:243–254 (1986).

Touitou, Y., et al., "Melatonin and the Pineal Gland," *Proceedings of the International Symposium on Melatonin and the Pineal Gland: From Basic Science to Clinical Application*, pp. 235–239 (Sep. 6–9, 1992).

Lisoni, P., et al., "Effect of an Acute Injection of Melatonin on the Basal Secretion of Hypophyseal Hormones in Prepubertal and Pubertal Healthy Subjects," *Acta Endocrinologica*, 111:305–311 (1986).

Cassone, V. M., et al., "Dose–Dependent Entrainment of Rat Circadian Rhythms by Daily Injection of Melatonin," *J. of Biol. Rhythms*, 1(3):219–229 (1986).

Arendt, J., et al., "The Effects of Chronic, Small Doses of Melatonin Given in the Later Afternoon on Fatigue in Man: A Preliminary Study," *Neuroscience Letters*, 45:317–321 (1984).

James, S.P., et al., "Melatonin Administration in Insomnia," *Neuropsych.*, 3(1):19–23 (1990).

Hoechst AG, "Melatonin Based Nasal Spray Compsn. for use as Sleep Inducer-Prep by Dissolving Melatonin, i.e. 5-methoxy-N-acetyl Tryptamine in Aq. Soln. Contg. Sodium Chloride," (From *Derwent Publications, Ltd.*, London, GB, Week 8040, 29 Apr. 1980, Abstract No. JP55057563.)

Lewy, A. J. et al *J. Neural Transm* (1986) Suppl. 21:311–322.

Lerner, A. B. and Nordlund, J. J. *Frontier of Pineal Physiology*, MIT Press (1975) pp. 42–43.

Palm, L., et al., "Correction of Non–24–Hour Sleep/-Wake Cycle by Melatonin in a Blind Retarded Boy", *Annals of Neurology*, 29(3):336–339 (1991).

Johnson, L. C., and Chernik, "D. A., Sedative–Hypnotics and Human Performance", *Psychopharm.* 76:101–113 (1982).

Johanson, C. E., and Uhlenhuth, E. H., "Drug Preference and Mood in Humans: Diazepam", *Psychopharm.* 71:269–273 (1980).

(List continued on next page.)

*Primary Examiner*—Shailendra Kumar
*Attorney, Agent, or Firm*—Lowe, Price, LeBlanc & Becker

[57] ABSTRACT

Methods of inducing sleepiness and sleep in an individual by administering to that individual a single dose of melatonin sufficient to induce sleepiness and sleep in the individual.

9 Claims, 16 Drawing Sheets

OTHER PUBLICATIONS

Hoddes, E., et al., "Quantification of Sleepiness: A New Approach", *Physcho Meth.*, 10(4):431–436 (1973).

Aldhous, M., et al., "Plasma concentrations of melatonin in man following oral absorption of different preparations", *Br. J. Clin. Pharmac.* 19:517–521 (1985).

Waldhauser, F., et al., "Sleep laboratory investigations on hypnotic properties of melatonin", *Psychopharm.*, 100:222–226 (1990).

Nickelsen, T., et al., "Influence of Subchronic Intake of Melatonin at Various Times of the Day on Fatigue and Hormonal Levels: A Placebo–Controlled, Double–Blind Trail", *J. of Pineal Res.*, 6:325–334 (1989).

MacFarlane, J. G., et al., "The Effects of Exogenous Melatonin on the Total Sleep Time and Daytime Alertness of Chronic Insomniacs: A Preliminary Study", *Biol. Psychiatry*, 30:371–376 (1991).

Wurtman, R. J. and Waldhauser, F., "Melatonin in Humans", Proc. of the First Int'l Congress on Melatonin in Humans, Vienna, Austria, Nov. 7–9, pp. 179–191 (1985).

Lewy, A. J., et al., "A complete PRC for melatonin administration in Humans", Abst. vol. 3, Society for Light Treatment and Biological Rhythms. p. 26 (1991).

Dollins, A. B., et al., "Effects on Ambient Illumination on Human Nocturnal Serum Melatonin Levels and on Sustained Performance", Abst. vol. 3, Society for Light Treatment and Biological Rhythms, p. 25 (1991).

Lewy, A. J., et al., "Immediate and Delayed Effects of Bright Light on Human Melatonin Production: Shifting Dawn and Dusk Shifts the Dim Light Melatonin Onset (DLMO)$^a$", In Wurtman, R. J., et al. *The Medical & Biol. Effects of Light. Annals of the New York Acad. of Sci. vol. 453 (1985)*.

Arendt, J., et al., "Some effects on melatonin and the control of its secretion in humans", *Photoperiodism, Melatonin and the pineal.*, Pitman, London (Ciba Found. Sym. 117), pp. 226–283 (1985).

Sack, R. L., et al., "Melatonin Administration to Blind People: Phase Advances and Entrainment", *J. of Biol. Rhythms* 6(3):249–261 (1991).

Folkard, S., et al., "Melatonin stabilises sleep onset time in a blind man without entrainment of cortisol or temperature rhythms", *Neuroscience Ltrs.*, 113:193–198 (1990).

Dahlitz, M., et al., "Delayed sleep phase syndrome resonse to melatonin", *The Lancet*, 337"1121–1124 (1991).

Ouichou, A., et al., "Delta–Sleep–Inducing Peptide Stimulates Melatonin, 5-Methoxytryptophol and Serotonin Secreteion from Perifused Rat Pineal Glands", *Biol Signals* 1:65–77 (1992).

Lieberman, H. R. and Lea, A. E., "Melatonin: effects on sleep and behaviour in man", *Melatonin Clinical Perspectives*, Oxford University Press, pp. 119–127 (1988).

Skene, D. J., et al., "Melatonin, Jet–Lag and the Sleep–Wake Cycle", *Sleep '88*, Edited by J. Horne, pp. 39–41 (1989).

James, S. P., et al., "The Effect of Melatonin on Normal Sleep", *Neuropsychopharmacology* 1 (1):41–44 (1987).

Lieberman, H. R., et al., "Effects of Melatonin on Human Mood and Performance", *Brain Research*, 323:201–207 (1984).

Arendt, J., et al., "Some effects of jet–lag and their alleviation by melatonin", Ergonomics 30(9):1379–1393 (1987).

Antón–Tay, F., "Melatonin: Effects on Brain Function", *Advances in Biochem. Psychopharm.* 11:315–324 (1974).

Morton, D. J. and Naik, D. "Effect of oral melatonin at various dose levels on blood pressure of normotensive humans", *Med. Sci. Res.* 17:837 (1989).

Carman, J. S., et al.,"Negative Effects on Melatonin on Depression", *Am. J. Psychiatry*, 133(10):1181–1186 (1976).

Reiter, R. J., "Melatonin: the chemical expression of darkness", *Mol. and Cell. Endoc.* 79:C153–C158 (1991).

Lewy, A. J., et al., "Light Suppresses Melatonin Secretion in Humans", *Science* 210:1267–1269 (1980).

Voordouw, B. C. G., et al., "Melatonin and Melatonin–Progestin Combinations Alter Pituitary–Ovarian Function in Women and Can Inhibit Ovulation", *J. of Clinical Endoc. and Metab.*, 74(1):108–117 (1992).

Antón–Tay, F., et al., "On the Effect of Melatonin upon Human Brain. Its Possible Therapeutic Implications", *Life Sciences* vol. 10, Part I, 841–850 (1971).

Strassman, R. J., et al. "Elevated rectal temperature produced by all–night bright light is reversed by melatonin infusion in men", *J. Appl. Physiol.* 71(6):2178–2182 (1991).

(List continued on next page.)

OTHER PUBLICATIONS

Paccotti, P., et al., "Effects of Exogenous Melatonin on Human Pituitary and Adrenal . . . Opposite Circadian stages in Men", *Chronobiologia*, 15:279–288 (1988).

Cagnacci, A., et al., "Amplification of pulsatile LH secretion by Exogenous Melatonin in Women", *J. of Clinical Endoc. and Metab.* 73(1):210–212 (1991).

Cagnacci, A., et al., "Melatonin: A Major Regulator of the Circadian Rhythm of Core Temperature in Humans", *J. of Clin. Endoc. & Metab.* 75(2):447–452 (1992).

Brezezinski, A., et al., "The Circadian Rhythm of Plasma Melatonin During the Normal Menstrual Cycle and in Amenorrheic Women", *J. Clin. Endocr. and Metab.*, 66:891–895 (1988).

Souétre, et al., "5-Methoxypsoralen Increases Evening Sleepiness in Humans: Possible Involvement of the Melatonin Secretion", *Eur. J. Clin. Pharm.* 36:91–92 (1989).

Vollrath, L., et al., "Sleep Induction by Intranasal Application of Melatonin", *Advances in the Biosciences* 29:327–329 (1981).

Lewy, A. J. and Sack, R. L., "Use of Melatonin to Assess and Treat Circadian Phase Disorders", 1993 Elsevier Science Publishers, B.V., 205–210.

Lewy, A. J., et al., "Melatonin Shifts Human Circadian Rhythms According to a Phase-Response Curve", *Chronobiol. Int.*, 9:380–391 (1992).

Dollins, A. B., et al., "Effect of pharmacological daytime doses of melatonin on human mood and performance", *Psychopharmacology*, Ms. No. 146, 1–7 (1993).

Dollins, A. B., et al., "Effects of Illumination on Human Nocturnal Serum Melatonin Levels and Performance", *Physiology & Behavior*, 53:153–160 (1993).

Lewy, A. J. et al., "Melatonin and the acute suppressant effect of light may help regulate circadian rhythms in humans", *Advances Pineal Res.* 5:285–293 (1991).

Tzischinsky, O., et al., "The importance of timing in melatonin administration in a blind man", *J. Pineal Res.*, 12:105 (1992).

Dollins, A. B., et al., "Effect on inducing nocturnal serum . . .. temperature, and performance", 1–28 (1993).

Tzischinksy, O., et al., Time-dependent effects of 5 mg melatonin on the sleep . . . function, *J Sleep Res.* 1 Abst. 468 (1992).

METHODS OF INDUCING SLEEP USING MELATONIN

RELATED APPLICATION

This application is a continuation-in-part of Ser. No. 07/955,304, filed Oct. 1, 1992, now abandoned, which is herein incorporated by reference.

BACKGROUND

Melatonin (N-acetyl-5-methyoxytryptamine) is a neurohormone secreted from the pineal gland. In mammals, including humans, melatonin is normally secreted in a circadian (or twenty-four hour) rhythm with blood levels of approximately 10 pg/ml during the daytime, with levels increasing to approximately 80–100 pg/ml during the nighttime. Peak secretion of melatonin occurs at around 2 AM. (Waldhauser, F. and Steger, H., PROCEEDINGS OF THE FIRST INTERNATIONAL CONGRESS ON MELATONIN IN HUMANS, pp. 179–191, Vienna, Austria, (Nov. 1985)). Studies have shown that secretion of melatonin is suppressed by bright light. (Lewy, A. J., et.. al., Science 210:1267–1269 (1980)).

Melatonin has a short biological half-life, and is rapidly metabolized by the liver. (Aldhous, M., et. al., Br. J. Clin. Pharm. 19:517–521 (1985)). Thus, doses up to 6.6 grams per day have been used to study the effects of melatonin in humans. Although, generally, no ill effects have been observed from the use of these very high doses, one recent study reports that ingestion of 300 mg of melatonin daily, for four months, resulted in inhibition of ovulation in women. (Bettie, C. G., et. al., J. Clin. Endocrin. Metabol. 74:108–117 (1992)).

No function has clearly been associated with melatonin in humans. In fact, lack of melatonin in humans has not been associated with any major abnormality. (Arendt, J., et. al., PHOTOPERIODISM, MELATONIN AND THE PINEAL, London, England (Ciba Foundation Symposium 117) pp. 266–283 (1985)).

SUMMARY OF THE INVENTION

The present invention relates to methods of inducing sleep in an individual by administering to that individual an effective dose of melatonin (i.e., a dose of melatonin which is sufficient to induce sleep). As used herein, sleep is defined as the state of rest characterized by relative physical and nervous inactivity, lessened responsiveness and unconsciousness. Sleepiness, as used herein, is defined as the subjective state which normally precedes sleep. Sleepiness is a good predictor of sleep.

The inducement of sleep by melatonin was measured as described herein, using standardized performance tests routinely used to evaluate the effects of melatonin, various hypnotics and sedatives (sleep-inducing substances), other pharmacologic agents and sleep loss. In particular, the art-recognized Stanford Sleepiness Scale was used for the quantification of sleepiness. Briefly, this scale contains seven descriptions ranging from "feeling active and vital; alert; wide awake" ($=1$) to "almost in reverie; sleep onset soon; lost struggle to remain awake" ($=7$).

The sleep-inducing effects of melatonin were also assessed as described herein, by a simple sleep test. Briefly subjects were asked to hold a positive pressure switch in each hand and to relax with eyes closed, while reclining in a darkened room. Latency and duration of switch release were measured as an indicator of sleep.

The methods of inducing sleep described herein involve the administration of an effective dose of melatonin to an individual in a single dose of short duration (i.e., an acute dose). In a preferred embodiment, administration of the single effective dose of melatonin to the individual is by oral ingestion. An effective dose of melatonin, as defined herein, is an amount of melatonin which induces sleep in an individual.

The single dose of melatonin administered to the individual is generally less than 10 mg, and, particularly, the dose of melatonin administered ranges from 0.1 to 1.0 mg of melatonin. Sleep test results indicate that acute administration of melatonin, in doses between 0.1 to 1.0 mg significantly decreased sleep onset latency and self-reported sleep latency, and increased sleep duration, relative to placebo. Surprisingly, a single, oral dose of melatonin within this range results in an acute rise in blood levels of melatonin to within normal physiological nocturnal melatonin levels. Plasma melatonin levels in humans are normally very low during most of the day (approximately 10 pg/ml). However, plasma melatonin levels rise sharply to a mean of approximately 45 pg/ml (range 0–200) between 0200 and 0400 h, slowly fall during normal hours of sleep and sharply fall around 0900 h. Administration of a single, oral dose of melatonin in the low dose range of 0.1 to 1.0 mg, results in an acute rise in circulating blood melatonin levels that remain within normal nocturnal physiologic range, as described herein, yet causes hypnotic effect (i.e., induces sleep). Doses of melatonin within the 0.1–1.0 mg range are herein referred to as physiological, or physiologic doses, as opposed to doses greater than 1.0 mg, which are referred to as pharmacological doses. Administration of physiologic doses of melatonin result in circulating blood levels of melatonin within physiologic ranges. Pharmacological doses of melatonin generally result in circulating blood levels of melatonin above the physiologic range.

The use of physiological doses of melatonin to induce sleep has a number of advantages over conventional chemical hypnotics, such as the drugs, benzodiazepines. Melatonin is naturally metabolized within hours of administration. Thus, methods of inducing sleep using melatonin, do not produce adverse residual effects the day following administration, as do conventional sleep-inducing drugs. Nor are the dangers of drug abuse and/or overdose, which are present with conventional chemical hypnotics likely. Moreover because melatonin is a naturally-occuring, endogenous substance, the doses of melatonin described herein would reasonably lack the potent amnesia-inducing effects of the benzodiazepines.

The effectiveness of low doses of melatonin to induce sleep, especially within the 0.1 to 1.0 mg range, and in particular, with doses as low as 0.1 and 0.3 mg, has not previously been demonstrated. The work presented herein demonstrates, for the first time that exogenous physiologic doses of melatonin, given in the daytime, acutely increase, or raise, blood melatonin levels to normal nocturnal levels. These physiologic doses of melatonin have a hypnotic effect on an individual (i.e., induces sleep in an individual). Surprisingly, the use of low, acute, physiologic doses of melatonin, as described herein, which induce sleep within minutes of administration, do not result in serum levels of melatonin outside of normal endogenous nocturnal ranges. Thus, exogenous, physiological doses of melatonin, used at times when it is appropriate, (i.e., when needed as a sleep-inducing aid) provides an effective method to induce sleep by acutely raising serum melatonin levels to normal physiological nocturnal levels.

BRIEF DESCRIPTION OF THE DRAWINGS

FIG. 5A depicts the Vigor-Activity scale. FIG. 5B depicts the Fatigue-Inertia scale. FIG. 5C depicts the Confusion-Bewilderment scale (N=20).

FIG. 7-7D depicts changes from baseline after ingestion of 0.1-10 mg of melatonin or placebo (N=3). FIG. 7D depicts changes in the Profile of Mood States Fatigue/Inertia Scale.

DETAILED DESCRIPTION OF THE INVENTION

Figure 1:
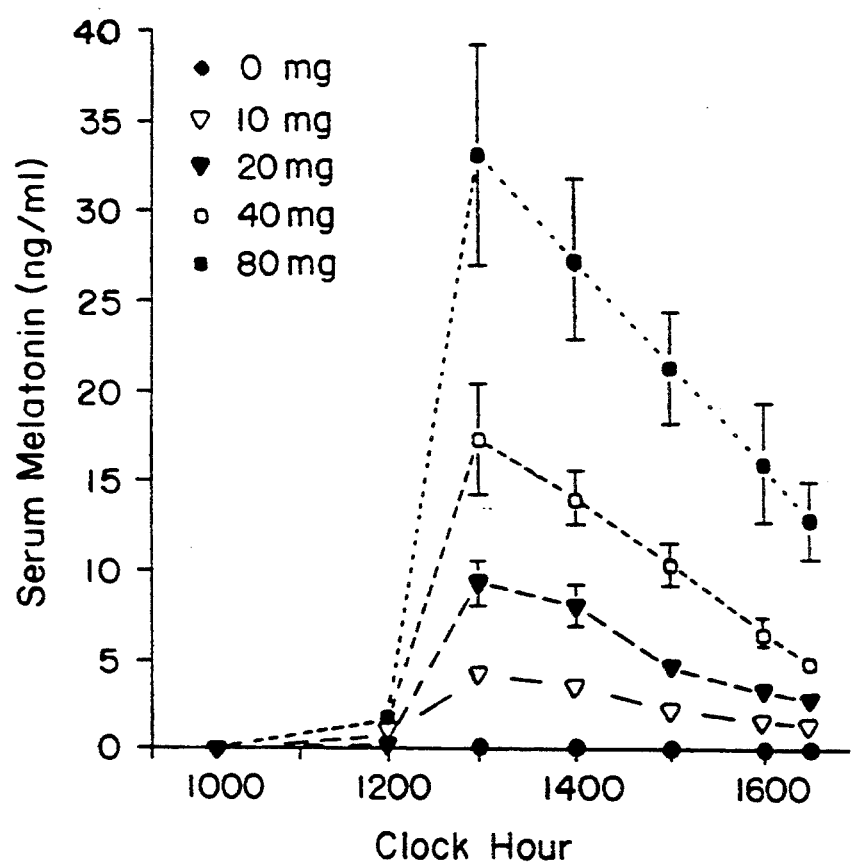
FIG. 1 depicts mean serum melatonin profiles of 20 subjects sampled at intervals after ingesting 10, 20, 40 and 80 mg of melatonin or placebo (N=20).

The present invention relates to methods of inducing sleepiness and sleep in an individual by administering to that individual a dose of melatonin sufficient to induce sleepiness and sleep (i.e., an effective dose). The methods, as described herein, involve the administration of melatonin in a single dose, the length of time of administration being within a short period (i.e, of short duration, or an acute dose). Typically, the single dose of melatonin is administered only when appropriate to induce sleep, as opposed to a sequential course of administration of melatonin over a number of days, or weeks. Thus, for example, an individual in need of a quick sleep-inducing aid is given a single dose of between 0.1-1.0 mg of melatonin. This exogenous dose of melatonin acutely raises the blood melatonin level to a normal nocturnal level averaging approximately 45 pg/ml, and, thus, induces sleep in the individual. The sleep inducing effect of low doses of melatonin is fast-acting, but not long-lasting (i.e., the blood levels of melatonin would not remain at nocturnal levels for more than a few hours). Importantly, blood melatonin levels fall back to within normal daytime levels after approximately seven hours. Thus, even though the acute dose of melatonin raises blood levels of melatonin to a concentration sufficient to induce sleep, the individual would awake, for example, the next day, with blood melatonin levels at the normal daytime levels, without any feelings of sleepiness.

The single dose of melatonin may be administered orally, parenterally (e.g., intracisternally, intraperitoneally), rectally, transdermally or nasally. In a preferred embodiment, administration of the single dose of melatonin is oral administration (ingestion). Single dose administration also includes subcutaneous time-release capsules, percutaneous patch and microsmatic pump. The form in which the melatonin will be administered (e.g., tablet, capsule, powder, solution, gel) will depend on the route by which it is administered.

The single dose of melatonin administered can be any dose of less than 10 mg of melatonin which is sufficient to induce sleepiness and sleep in the individual. In particular, the dose of melatonin administered ranges from 0.1 to 1.0 mg. In a preferred embodiment, the dose of melatonin is 0.3 or 0.1 mg. These low doses of melatonin are referred to as physiological doses. Physiological doses of melatonin generally do not elevate blood melatonin levels above normal endogenous levels of melatonin.

Surprisingly, administration of these low doses of melatonin does not raise blood melatonin levels above the normal physiological nocturnal range, yet are effective in inducing sleep in an individual. A single dose of less than 1.0 mg of melatonin results in blood levels of melatonin within normal nocturnal levels averaging approximately 45 pg/ml (range 0–200 pg/ml). Thus, the administration of a single physiological dose of melatonin, (e.g., between 0.1-1.0 mg), which results an acute rise in circulating blood melatonin levels to within the physiological nocturnal range induces sleep in an individual.

In humans, no known function has been clearly associated with melatonin. Oscillations in plasma melatonin levels could constitute a time signal, affecting the temporal characteristics of circadian rhythms or a means of communicating information about environmental lighting (and thus time of day) to the brain and other organs, thereby mediating changes in animal physiology and behavior, particularly those associated with photoperiodism or seasonality. Researchers have described the use of melatonin to retrain circadian rhythms by administering acute pharmacologic doses (e.g., 50 mg or more, of melatonin) or repeated daily pharmacologic doses (e.g., 5 mg of melatonin). For example, melatonin has been evaluated for its effectiveness in the synchronization of circadian, or 24 hour, rhythms, such as the rest/activity cycle (Palm, L. et. al., *Annals of Neurol.* 29:336-339 (1991)) and as a treatment for jet-lag (Arendt, J. et. al., *Ergonomics* 30:1379-1393 (1987)). Melatonin has also been used to help humans to adapt to other situations where disturbances in circadian rhythms occur (e.g., insomnia, seasonal affective disorder, blindness and old age). (Skene, D. J., et. al., Sleepiness '88, ed. J. Horne, pp. 39–41, Gustav Fischer Verlag, New York (1989)).

Other possible biological roles for melatonin that have been investigated include the regulation of ovarian function, (Bettie, C. G., et. al., *J. Clin. Endocrinol. Met.* 74:108–117 (1992)); blood pressure (Morton, D. J. and Naik, D. *Med. Sci. Res.*, 17:837 (1989)); and depression (Carman, J. S., et. al., *Am. J. Psychiatry*, 133:1181–1186 (1976)). Some studies suggest a role for melatonin in human development. The decrease in amplitude of the melatonin rhythm which occurs in the first decade of life has been proposed as a factor contributing to pubescence (Waldhauser, F., et al. *Lancet*, 1:362–265 (1984). Further decrease, after the sixth decade, may contribute to the disruptions in circadian rhythmicity reported by the elderly. (Czeisler, C. A., et al., *Lancet*, 340:933–936 (1992)).

Alternately, the physiological significance of variations in plasma melatonin levels may be due to its hormonal effects, such as reduction in core body temperature via thermoregulation (Cagnacci, A., et. al., *J. Clin. Endocrin. Met.*, 75:447–452 (1992)); increase in brain levels of norepinephrine, dopamine and seratonim (Wendel, O. T., et al., *Experimentia*, 15:1167–1168 (1990); Fang, J. M., and Dubocovich, M. L., *FASEB J.*, A1802 (abstr.) (1988); or the stimulation of prolactin secretion (Waldhouser, F., et al., *Neuroendocrinology*, 46:125–130 (1987)).

Studies have also been performed to evaluate the tranquilizing, or sleep-inducing effects of melatonin, using very high doses or doses administered over a number of days (i.e., chronic administration). Pharmacologic doses of melatonin have been used in these studies because of the belief that rapid metabolization of melatonin would render low doses ineffective. These pharmacologic doses of melatonin used raised plasma melatonin levels well beyond the normal nocturnal range. For example, one study found that a dose of 240 mg given over a two-hour period raised plasma melatonin levels several thousand fold. (Lieberman. H. R., et. al., *J. Psychiatric Res.*, 17:134–145 (1984). Results of these studies are inconclusive as to the effectiveness of melatonin as a sleep-inducing aid. (Nickelsen, T., et. al., *J. Pineal Res.*, 6:325–334 (1989)); (MacFarlane, J. G., et. al., *Biol. Psychiatry*, 30:371–376 (1991)); (Arendt, J. et. al., *Neurosci. Lett.*, 45:317–321 (1984)); and (James, S. P., et. al., *Neuropsychopharm.*, 1:41–44 (1987)).

Alternate routes of administration, such as intranasal (nasal sprays) or intraocular (eye drops) have also been tried to avoid rapid metabolization of melatonin in the liver, and thus make it possible to use lower doses of melatonin. One study (Vollrath, L., et. al., ADVANCES IN BIOSCIENCES, vol. 29, pp. 327–329 (1981)) reported that intranasal administration of 1.7 mg of melatonin induced sleep onset.

It is important to distinguish the role of melatonin in inducing sleep (i.e., a sleep-inducing aid) from the role of melatonin as a time signal used to re-set circadian rhythm. The endogenous circadian rhythm of humans under "free-running" conditions is about 25 hours. Thus, the sleep/wake cycle needs to be continuously reset (resynchronized) to the appropriate 24 hours. Melatonin, administered chronically (i.e., on a daily basis over a number of days, weeks or even months) has been shown to entrain, or resynchronize, the sleep/wake cycle to the 24 hour day length. (Palm, L. et. al., *Annals of Neurol.* 29:336–339 (1991)).

However, as described herein, it has been demonstrated for the first time that a single physiologic dose of melatonin is effective to acutely raise serum melatonin levels to normal nocturnal levels and, thus, induce sleep in an individual. As defined herein, the dose of melatonin required to increase circulating blood melatonin to normal nocturnal levels of melatonin is a physiologic dose. Moreover, the acute nature of melatonin's hypnotic effect suggests that it is a direct physiological effect which is unrelated to previously reported circadian effects. In general, the effective dose of melatonin (i.e., an amount of melatonin which induces sleep) is a concentration of melatonin below 1.0 mg, and, preferably 0.3 or 0.1 mg. The inducement of sleep resulting from the effective dose of melatonin is rapid, occurring within 2 hours after ingestion and no residual effects were reported by subjects tested. Thus, the method described herein, is extremely useful to induce sleep in individuals interested in, or in need of, fast-acting sleep-inducing aids. Furthermore, because the doses of melatonin used in the methods described herein are physiological doses, which do not result in blood melatonin levels above normal physiological levels, even long term use of the present method should be reasonably safe.

As described in detail in Example 1, twenty male subjects participated in Study I which tested the sleepiness- and sleep-inducing effects of a single oral dose of 10 to 80 mg of melatonin. The study was double-blind and placebo-controlled. A repeated measures, within subjects $5 \times 5$ Latin Square design was employed. The subjects participated in five 7.5 hour (0930–1700 h) testing sessions. At least five days elapsed between successive test sessions. Capsules containing .10, 20, 40, or 80 mg of melatonin or placebo were administered (p.o.) at 1145 h of each test day. This time of day was chosen for melatonin administration because midday endogenous blood levels of melatonin are normally very low, or even undetectable. Thus, it was reasonable to conclude that the results obtained in these studies (i.e., the inducement of sleepiness and sleep) were due to the exogenous melatonin administered.

On admission, a catheter with a heparin lock was implanted in a forearm vein for blood sample withdrawal. Blood samples were taken from each volunteer at 1000, 1200, 1300, 1400, 1500, 1600 and 1630 h. Serum samples were separated by centrifugation and stored at $-20°$ C. until they could be assayed for melatonin concentration as described in Example 2. Oral temperature, blood pressure, and heart rate, and sleepiness were assessed hourly.

The subjects were required to sit at an assigned computer workstation, with eyes open, and to complete interactive computer tasks throughout the day. Performance tasks and mood inventories that previous studies have shown to be sensitive to the effects of melatonin, various hypnotics, other pharmacologic agents, and sleep loss were used, as described in Example 3, to determine the effects of the melatonin administration. A brief description of the tasks is as follows.

A slightly modified version of the *Wilkinson Auditory Vigilance Task* was used to measure simple auditory vigilance. *Dual Task Information Processing* was measured by combining the Bakan vigilance test with the "estimation of two classes of events in a signal stream" (PROP) test to assess sustained, complex information processing. The *Four-choice Visual RT* was used to measure visual vigilance. The *Simple Auditory RT* was used as it has been proven to be sensitive to the effects of neurotransmitter precursors and foods that may alter central precursor availability. The *Digit Symbol Substitution Task*, taken from the Weschler IQ test and adapted for computerized administration was used and has been reported to be sensitive to a variety of factors. The *Profile of Mood States* (POMS) and *Stanford Sleepiness Scale* (SSS) were used to measure the subjects' mood and sleepiness throughout testing.

The POMS questionnaire and the Digit Symbol Substitution, Four Choice RT; and Simple Auditory RT tasks were administered at 1030, 1300, 1500, 1700 h. The Wilkinson Auditory Vigilance task was administered at 1200 and 1400, and the Dual task was administered at 1300 and 1500 h. The SSS was completed at 1030 and hourly after 1200.

The mean serum melatonin levels of Study I are illustrated in FIG. 1. The mean (SEM) areas under the time-melatonin-concentration curve (AUC) between 1000 and 1640 h for the placebo, 10, 20, 40 and 80 mg treatment conditions were 60 (1.5), 12228 (5746.1), 27186 (14268.8), 52557 (26401.6), and 106223 (63038.3) pg/ml, respectively. Serum melatonin AUC, roughly proportional to dose, differed significantly among the five treatment conditions $[F(4,60)=42.67, p<0.001]$ and all planned contrasts were significant $(p<0.01)$. The order and treatment by order effects were not significant.

Figure 2:
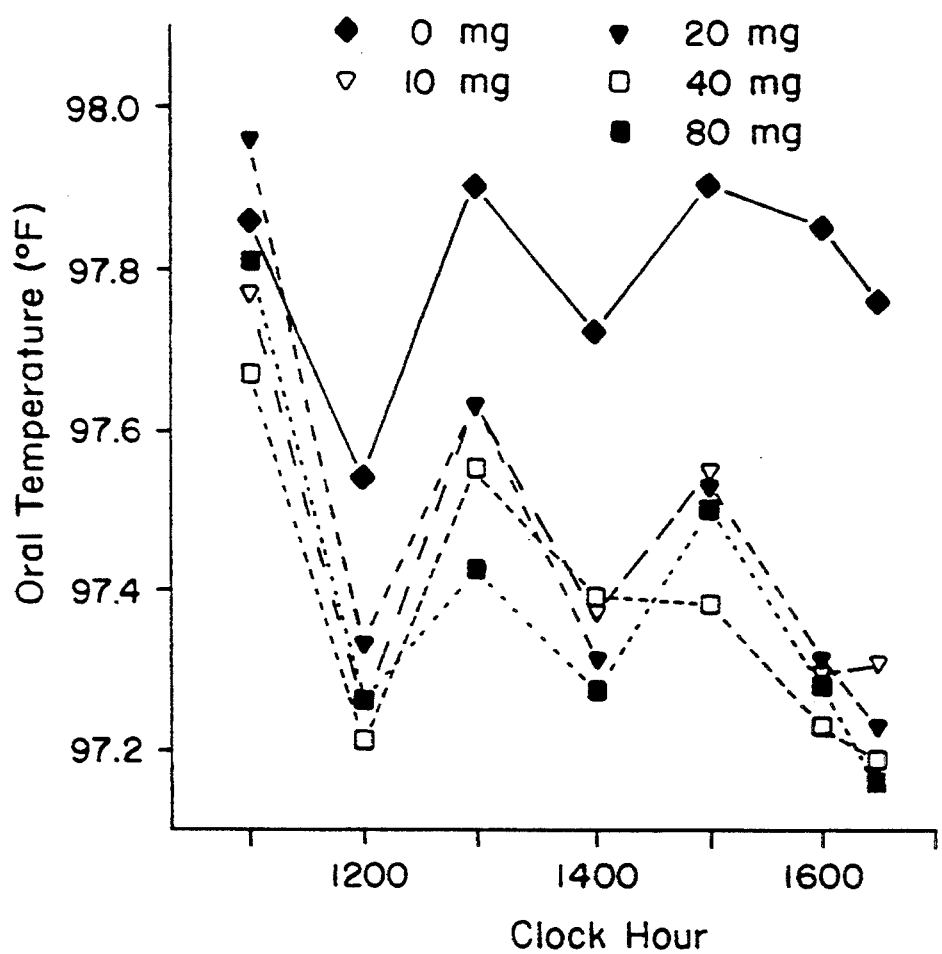
FIG. 2 depicts mean oral temperatures measured at intervals throughout the day after ingesting melatonin or placebo (N=20).

The mean oral temperatures of Study I, measured under each treatment condition are illustrated in FIG. 2. Oral temperature changed significantly with both treatment and time $(F(4,60)=11.81, p<0.001; F(4,60)=7.69, p<0.001$, respectively). Contrasts indicate that oral temperature measured during the placebo treatment were an average of 0.45° F. higher than those measured during the melatonin treatments $(F(5,15)=4.91, p<0.007)$. No significant dose-related differences in oral temperature were found among the melatonin treatments.

Figure 3:
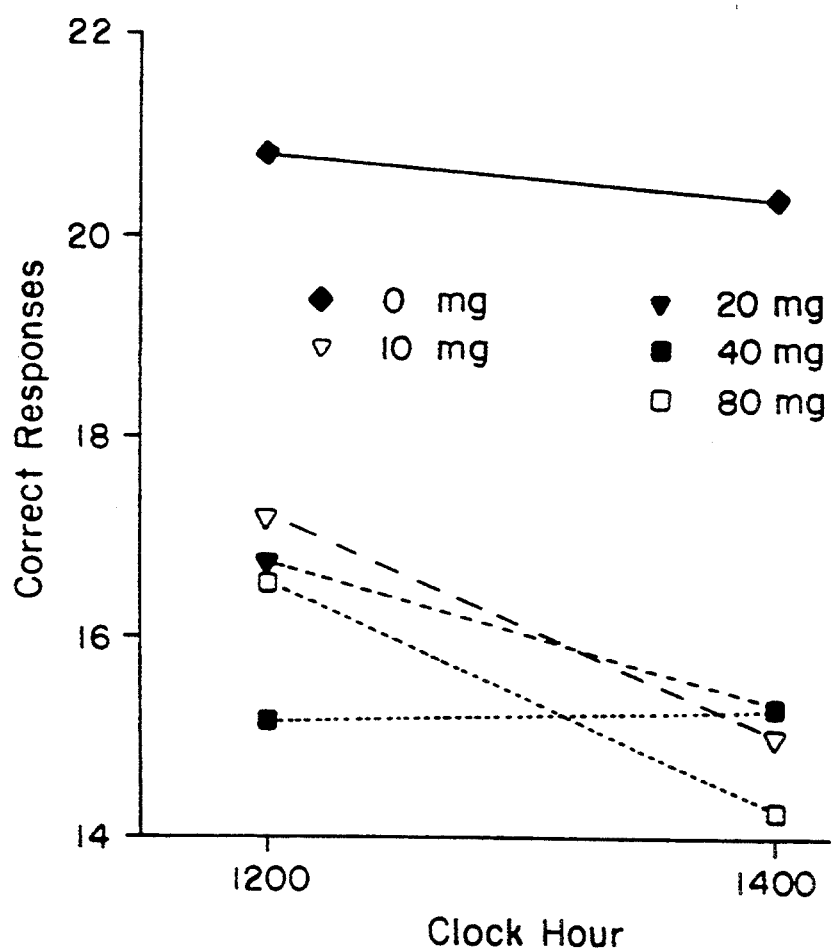
FIG. 3 depicts mean number of correct responses on the Wilkinson Auditory Vigilance Task after ingesting melatonin or placebo (N=20).

While all of the melatonin doses administered were effective in producing performance changes, the observed changes were not proportional to the doses used in Study I. The number of Wilkinson Auditory Vigilance Task correct responses decreased significantly with melatonin ingestion, as illustrated in FIG. 3 $(F(4,60)=8.91, p<0,001)$. Contrasts indicate that there were significantly fewer correct responses during melatonin treatment than during placebo treatment $(\Delta 4.89, p<0,001$, wherein $\Delta$ is defined as "a change of"). Other contrasts on this measure were significant, but the range of differences among the number of correct response means was quite small ($\Delta 0.9$). Mean Four Choice RT latencies increased significantly during melatonin treatment $(F(4,60)=4.19, p<0.005)$. Contrasts indicate that the mean RT increased from 374.85 ms during placebo treatment to 392.81 ms during melatonin treatment $(F(5,15)-7.28, p<0,001)$.

Figure 4:
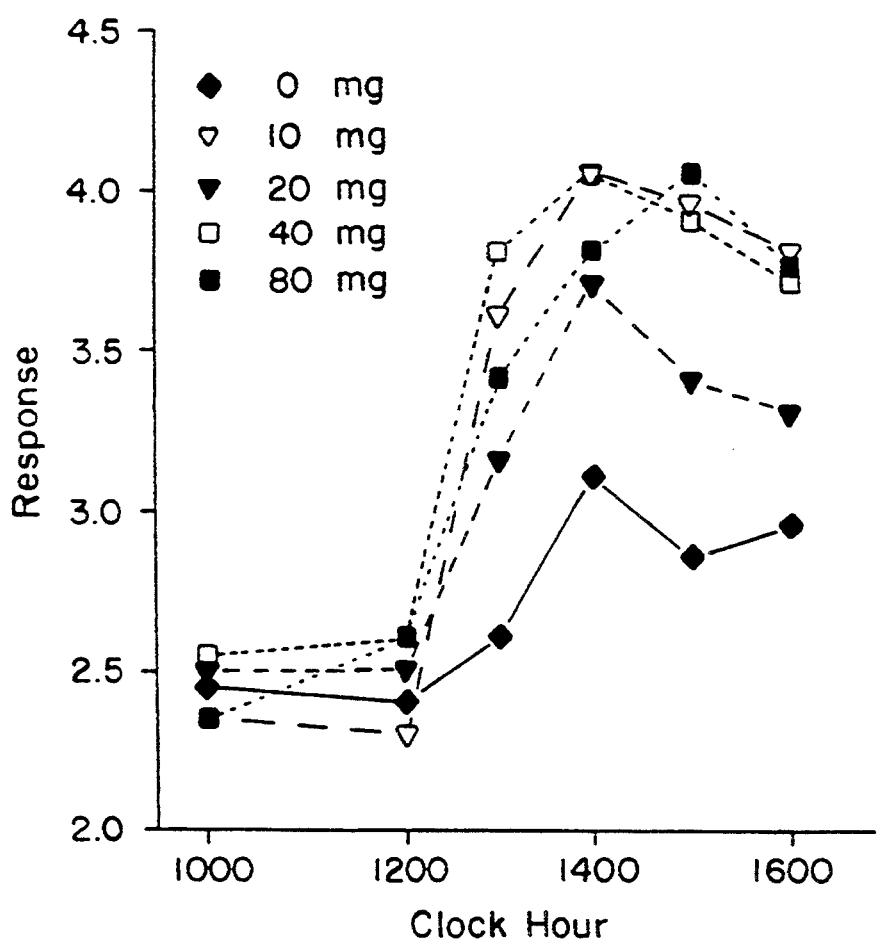
FIG. 4 depicts mean response scores to the Stanford Sleepiness Scale (SSS) throughout testing (increased sleepiness is indicated by higher scores, N=20).

Stanford Sleepiness Scales responses indicated that subjects were significantly more fatigued when taking melatonin, as illustrated in FIG. 4 $(F(4,60)=6.11, p<0.001)$. Contrasts indicate that the mean response score of 2.87, measured during placebo treatment, was significantly lower than the 3.71 measured during melatonin treatment $(F(5,15)=3.11, p<0.040)$.

Figure 5A:
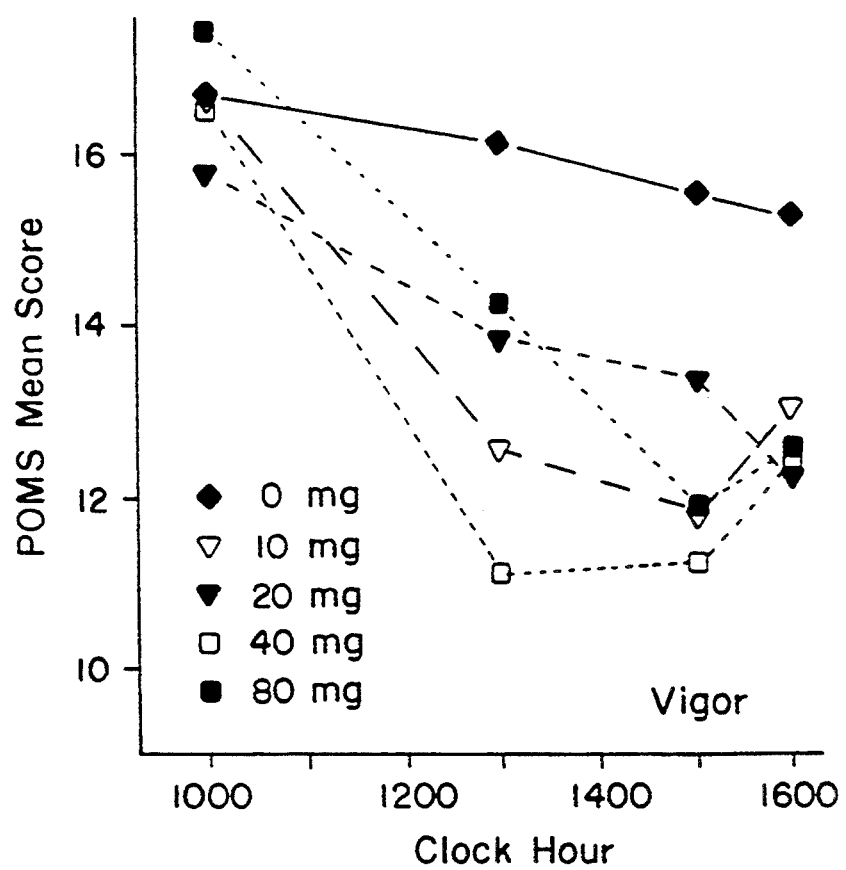
FIG. 5A-5C depicts mean response scores on the Profile of Mood States (POMS) questionnaire.
Figure 5B:
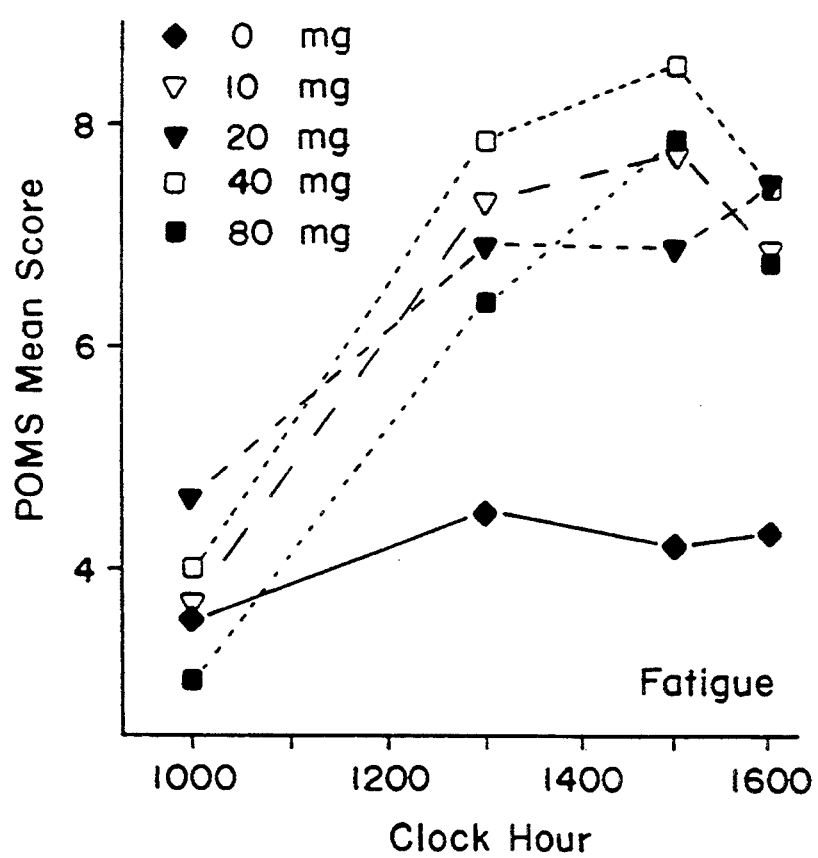
Figure 5C:
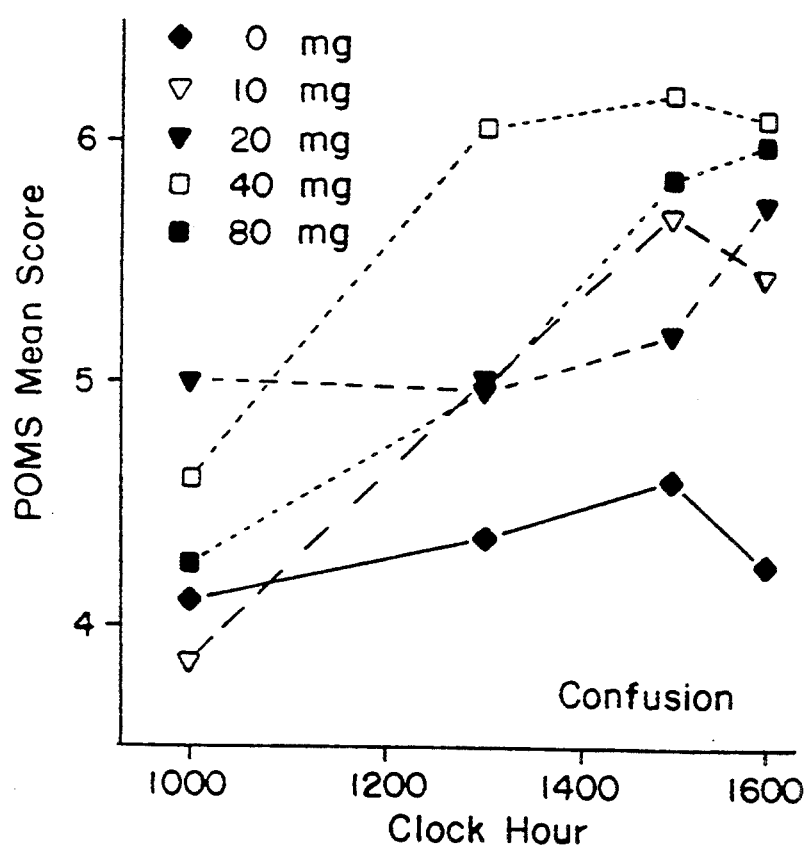

Subjects' POMS responses indicate that melatonin treatment (versus placebo) caused significant differences in feelings of Vigor, Fatigue, and Confusion, as illustrated in FIG. 5 $(F(4,60)=4.25, p<0.004; F(4,60)=4.11, p<0,005; F(4,60)=2.83, p<0.032$, respectively). Contrasts indicate that subjects felt more Vigorous and less Fatigued when taking placebo than when taking melatonin. Mean placebo/melatonin response differences for the subject responses on the Vigor and Fatigue scales were $\Delta 3.13$ $(F(5,15)-4.60, p<0.01]$ and $\Delta 3.00$ $(F(5,15)=5.01, p<0.007)$ respectively. Placebo/melatonin contrasts on the Confusion scale approached significance $(p<0.053)$.

Order effects of Study I were as follows. The number of correct and incorrect responses measured on the Dual and Wilkinson Auditory Vigilance Tasks decreased significantly on successive test days. The number Four Choice RT responses and the latency of those responses decreased significantly on successive test days. The number of correct responses measured during the Digit-Symbol Substitution Task increased significantly on successive test days. No significant order effects were found for the remaining measures.

These data indicate that ingestion of melatonin in a single dose of 10 to 80 mg significantly decreases oral temperature, feelings of Vigor, and number of correct responses on the Wilkinson Vigilance Task, relative to placebo ingestion at the same time. Administration of a single, oral dose of melatonin of 10 to 80 mg also increased feelings of Sleepiness, Fatigue, and Confusion, as well as Four Choice RT response latency.

As described in detail in Example 4, three subjects were selected for participation in Study II, which tested the sleepiness- and sleep-inducing effects of a single, oral dose of less than 10 mg of melatonin. Treatment conditions were also double-blind and placebo-controlled. A repeated measures, within subjects, 5×5 Latin square design was employed, with subjects randomly assigned to the first, third and fifth row of the square.

Each subject participated in five 8.0 hour (h) (0930–1730 h) test sessions, at least five days apart. Capsules containing 10.0, 1.0, 0.3, or 0.1 mg of melatonin or placebo were administered at 1145 h of each test day. Treatment order was determined by the Latin square design.

On admission, a catheter with a heparin lock was implanted in a forearm vein for blood sample withdrawal. Blood samples were taken from each volunteer at 1000, 1200, 1300, 1400, 1500, 1600, 1700, and 1730 h and analyzed for melatonin as described in Example 2. Body temperature was assessed hourly.

Figure 6:
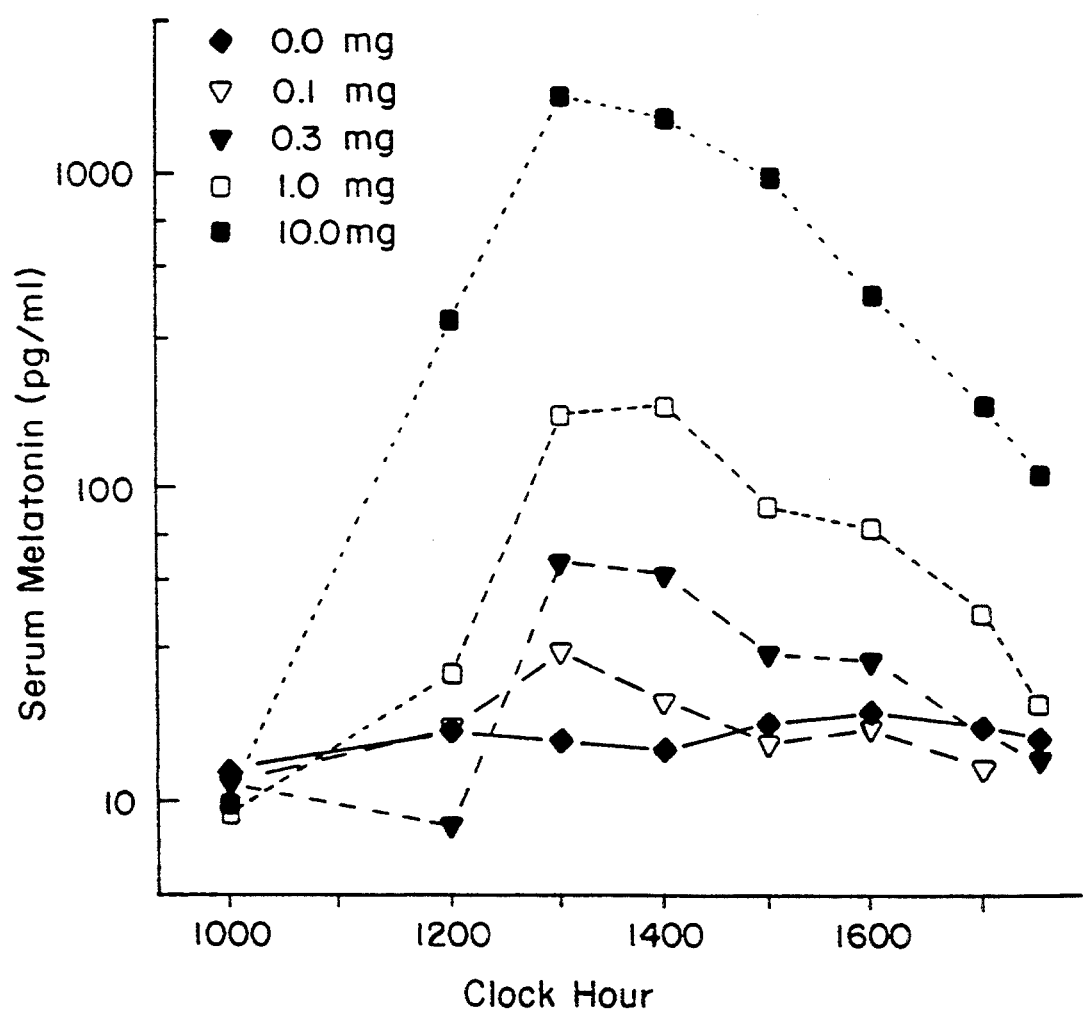
FIG. 6 depicts the mean serum melatonin levels of three healthy male subjects following ingestion of 0.1, 0.3, 1.0 and 10.0 mg of exogenous melatonin (assay sensitivity 8 pg/ml).

The mean serum melatonin levels are illustrated in FIG. 6. The mean (SEM; N=3) areas under the time-melatonin-concentration curve (AUC) between 1000 and 1740 h for the 0.1, 0.3, 1.0, and 10.0 mg melatonin doses and placebo were 130 (9.74), 204 (9.11), 591 (84.08), 5265 (668.08), and 119.50 (26.98) respectively (assay sensitivity=8 pg/ml). Mean (SEM) peak serum melatonin levels occurred at 1300 h and were 15 (4.46), 29.33 (7.98), 57 (0.71; N=2, outlier omitted), 170 (47.01), and 1748 (137.99) pg/ml for the placebo, 0.1, 0.3, 1.0 and 10.00 mg treatment conditions respectively. It is important to note that the peak increase observed after the 0.1 and 0.3 mg doses were within the normal physiological nocturnal range for serum melatonin levels.

Figure 7A:
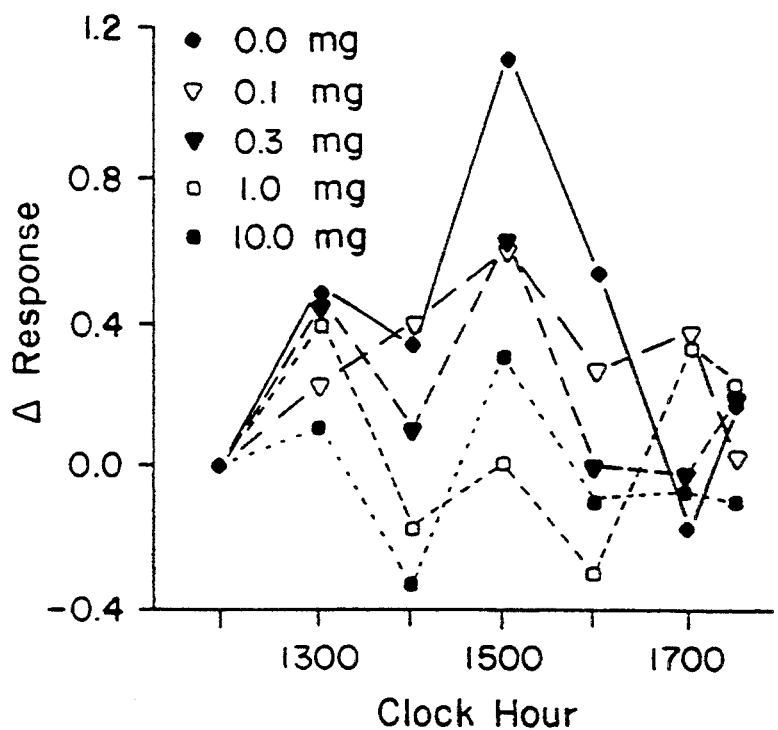
FIG. 7A depicts changes in oral temperature.
Figure 7B:
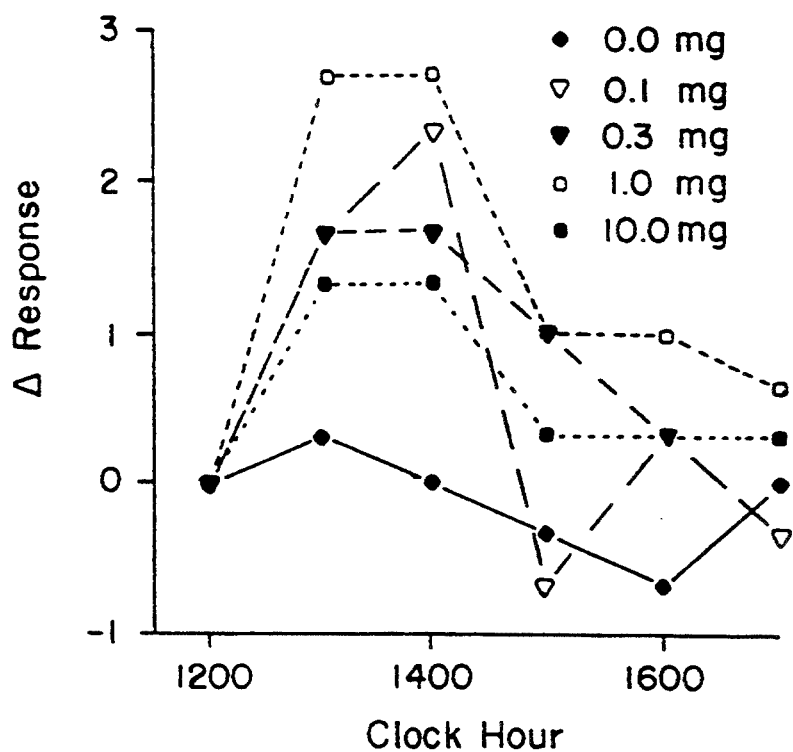
FIG. 7B depicts changes measured by the Stanford Sleepiness Scale (SSS).

The mean changes (1300 to 1730 h minus 1200 h baseline; N=3) in oral temperature and subjective sleepiness, measured in response to melatonin (0.1, 0.3, 1.0, and 10.0 mg) or placebo treatments, are illustrated in FIG. 7A and 7B respectively. Between 1300 and 1600 h, the normal afternoon circadian increase in oral temperature was reduced by all of the melatonin treatment conditions, but not by placebo. Feelings of sleepiness and sleep as measured by the Stanford Sleepiness Scale, were increased by melatonin ingestion during the same period.

Figure 7C:
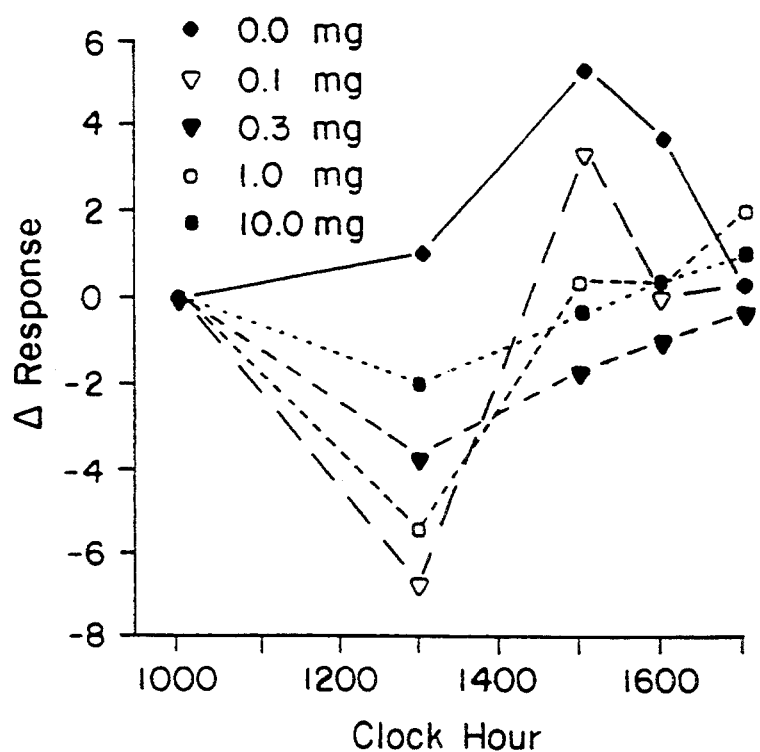
FIG. 7C depicts changes in the Profile of Mood States Vigor/Activity Scale.
Figure 7D:
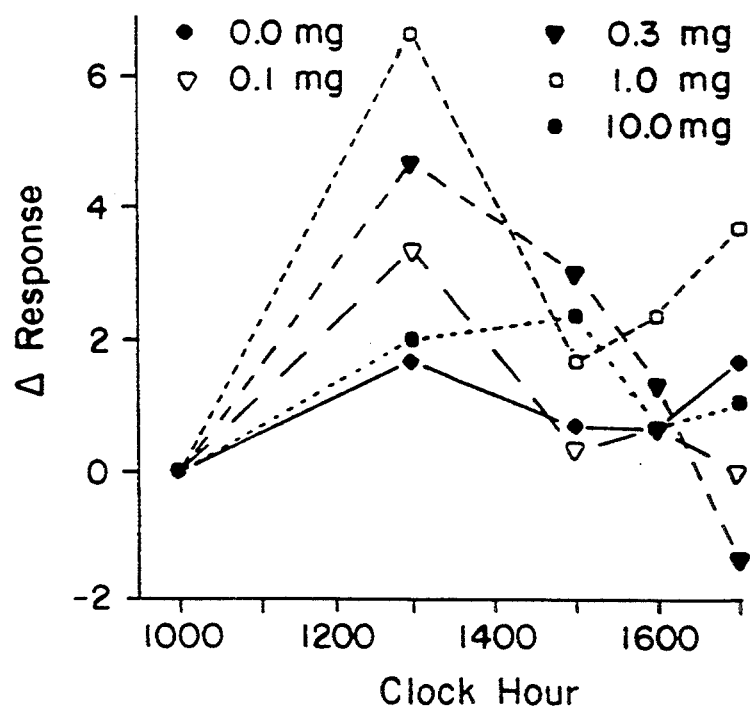

The mean response changes (1300 to 1700 h minus 1000 h baseline; N=3) in the Profile of Mood States (POMS) Vigor/Activity and Fatigue/Inertia scales are illustrated in FIG. 7C and 7D respectively. These responses indicate that the subjects felt more sleepiness when ingesting melatonin, with the greatest placebo vs melatonin difference occurring at 1300 h. The mean (SEM) Vigor/Activity scale responses when ingesting placebo or melatonin (0.1, 0.3, 1.0, or 10.0 mg) at 1300 h were 1.0 (3.56), −6.7 (2.13), −3.67 (1.91), −5.33 (0.98), and −2.0 (2.49) respectively. The Fatigue/Inertia scale response peaks were also measured at 1300 h. The means peak (SEM) values were 1.7 (3.3) , 3.3 (1.0) , 4.7 (1.2), 6.7 (1.9) , and 2.0 (2.4) in response to placebo or 0.1, 0.3, 1.0 or 10.0 mg of melatonin, respectively.

These data show that oral administration of melatonin in doses of less than 10 mg (e.g., 0.1 to 1.0 mg) also significantly decreased oral temperature, feelings of vigor and number of correct responses on the Wilkinson Vigilance Task, relative to placebo ingestion at the same time. Yet, surprisingly, a single dose of melatonin between 0.1 and 0.3 mg did not result in blood melatonin levels outside of normal physiological nocturnal ranges. Thus, exogenous melatonin, administered orally in doses that result in normal physiological nocturnal levels, is sufficient to induce sleepiness and sleep as measured by standard performance tests.

It is important to note that the subjects of both studies described herein were not permitted to actually fall asleep. Investigators monitored the subjects throughout the administration of the performance tasks to ensure that the subjects did not close their eyes or sleep. This was necessary to maintain the experimental protocol as designed and provide a means of comparison of the melatonin doses used in these studies and other studies using melatonin, and other various hypnotics, based on the standardized performance tests described in Example 3. However, it is reasonable to presume that, absent the investigator's intervention, the subjects of the study described herein would have fallen asleep.

Study III expanded the observations of Study II. In Study III, the effects of low doses of melatonin (0.1-10 mg p.o.) or placebo, administered at 1145 h, on sleep latency and duration; mood; performance; oral temperature; and serum melatonin levels using 20 healthy male volunteers were examined. A repeated-measure double-blind Latin Square sign was used. As described in detail in Example 5, subjects completed a battery of interactive computer tasks designed to asses performance and mood between 0930 and 1700 h on each of five separate occasions. The sequence and timing of events were held constant on each day.

The sleep-inducing effects of melatonin were assessed via a simple sleep test. At 1400 h, subjects were asked to hold a positive pressure switch in each hand and to relax with eyes closed, while reclining in a quiet darkened room, and the latency and duration of switch release, an indicator of sleep, were measured. Areas under the time-melatonin concentration curve varied in proportion to the various melatonin doses ingested, and the 0.1 and 0.3 mg doses generated peak serum melatonin levels which were within the normal nocturnal melatonin range in untreated people. All melatonin doses tested significantly increased sleep duration, as well as self-reported sleepiness and fatigue, relative to placebo. Moreover, all of the doses significantly decreased sleep onset latency, oral temperature and the number of correct responses on the Wilkinson Auditory Vigilance task. These data suggest that normal nocturnal serum melatonin levels produced in the daytime by ingestion of melatonin have sleep inducing properties. They also raise the possibility that the physiological increase in serum melatonin levels which occurs around 11 pm constitute a signal which participates in normal sleep onset.

Figure 8:
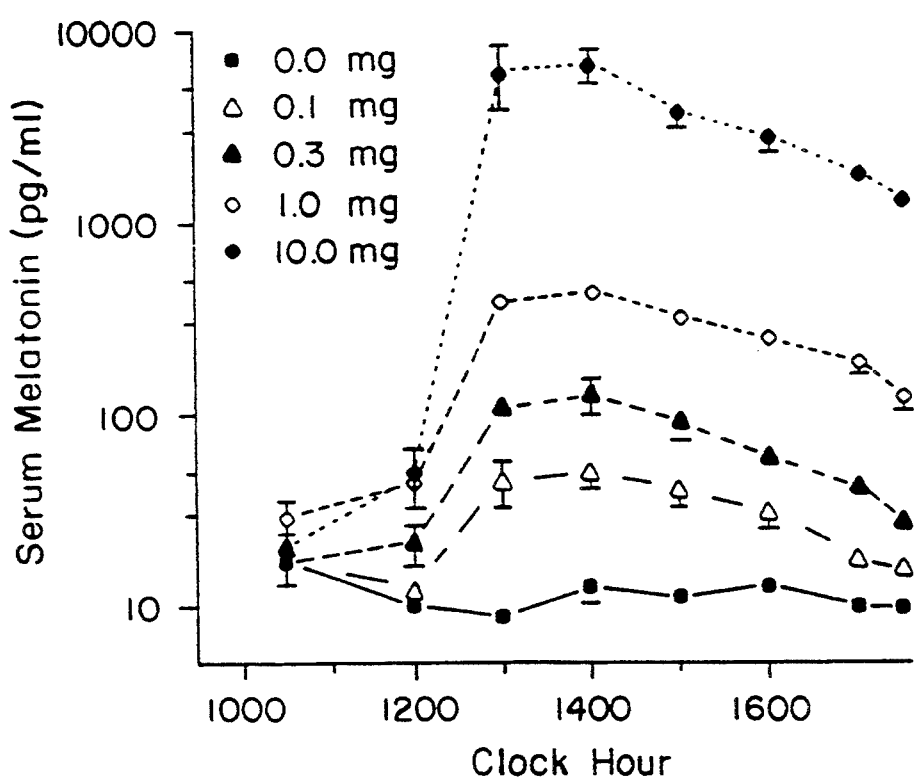
FIG. 8 depicts mean serum melatonin profiles of 20 subjects sampled at intervals after ingesting 0.1-10 mg of melatonin or placebo at 1145 h.

The mean serum melatonin levels as measured for the Study III subjects are illustrated in FIG. 8. The mean (SEM) areas under the time-melatonin-concentration curve (AUC) between 1000 and 1730 h for the placebo, 0.1, 0.3, 1.0, and 10 mg treatment conditions were 87.7 (5.11), 213.2 (25.02), 459.9 (62.7), 1599.0 (141.7) and 21000 (3752.3) pg/ml, respectively. Serum melatonin AUC differed significantly among the five treatment conditions [$F$ 4,60=34.34, $p<0.001$] and all planned contrasts were significant ($p<0.001$). The order and treatment by order effects were not significant. Serum melatonin concentrations observed following the 0.1 and 0.3, mg doses were within the normal nocturnal dynamic range of melatonin concentrations.

Figure 9A:
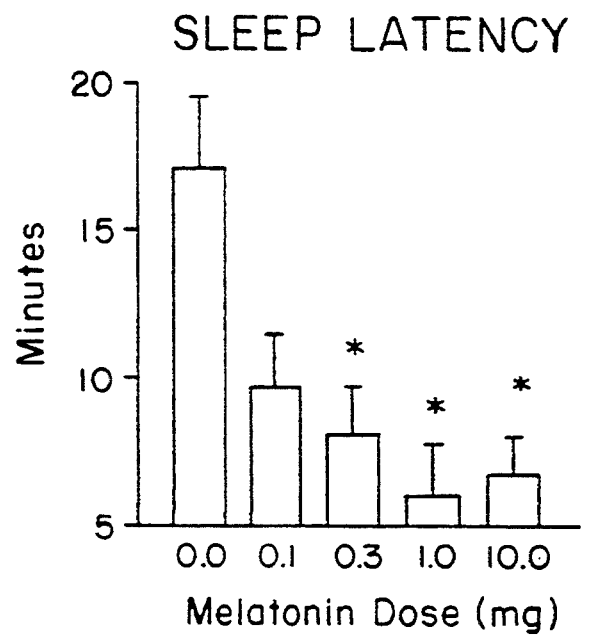
FIG. 9A-9D depicts mean (SEM) sleep onset latencies, sleep durations, self-reported sleep onset latencies, and post-test Standard Sleepiness Scale responses following ingestion of 0.1-10.0 mg of melatonin or placebo at 1145 h (N=20).
Figure 9B:
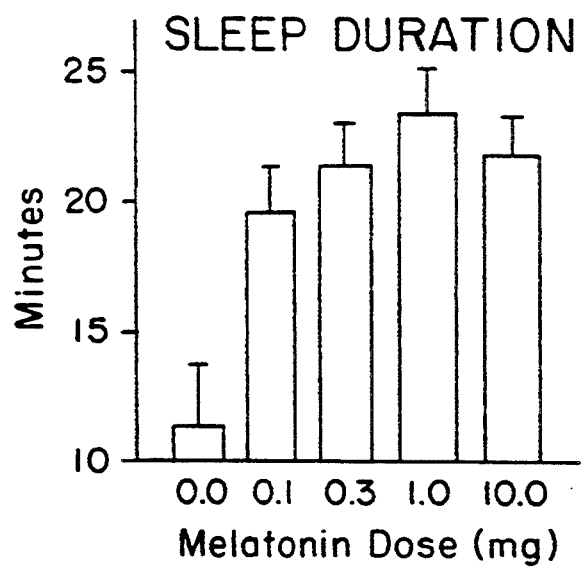
Figure 9C:
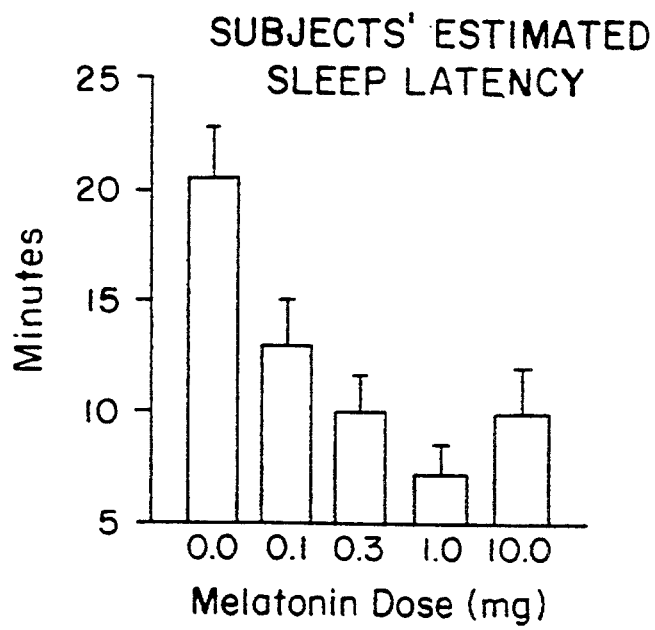
Figure 9D:
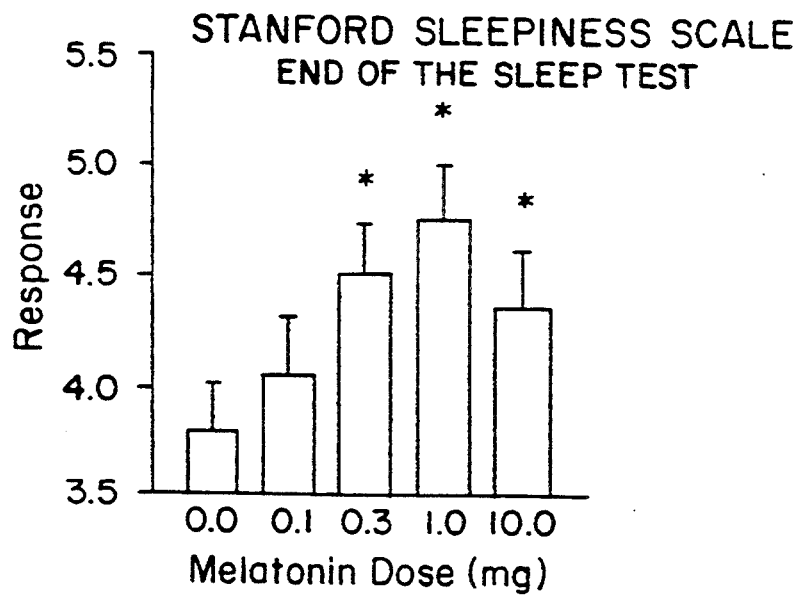
Figure 10A:
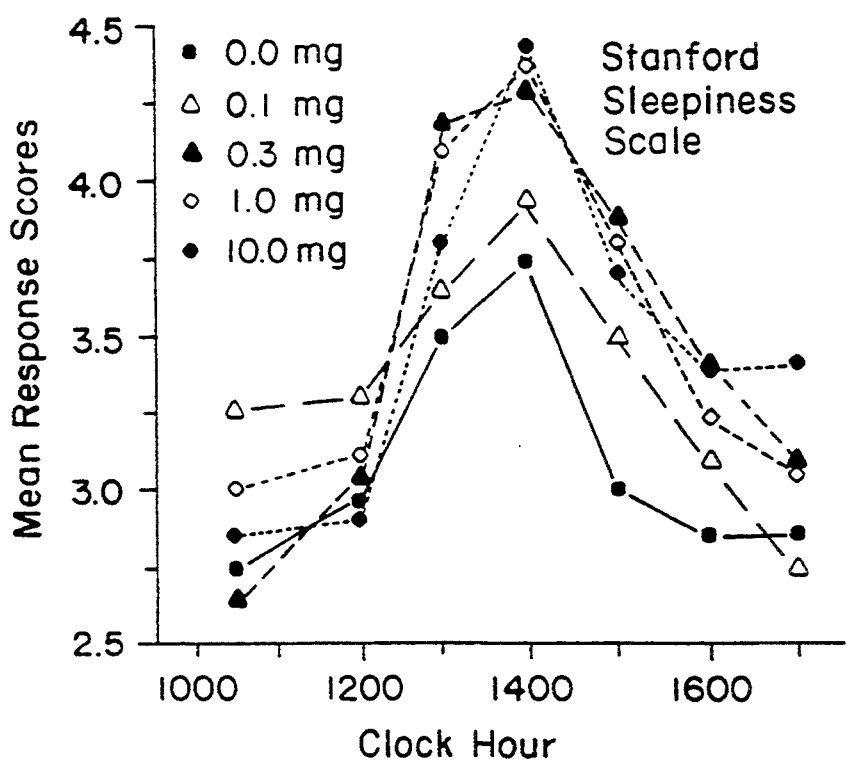
FIG. 10A-10C depicts mean response scores on the Stanford Sleepiness Scale, POMS Vigor-Activity, and POMS Fatigue-Inertia scales throughout testing. 0.1-10 mg of Melatonin or placebo was ingested at 1145 h (N=20). Increased feelings of sleepiness, vigor, and fatigue are indicated by higher scores.
Figure 10B:
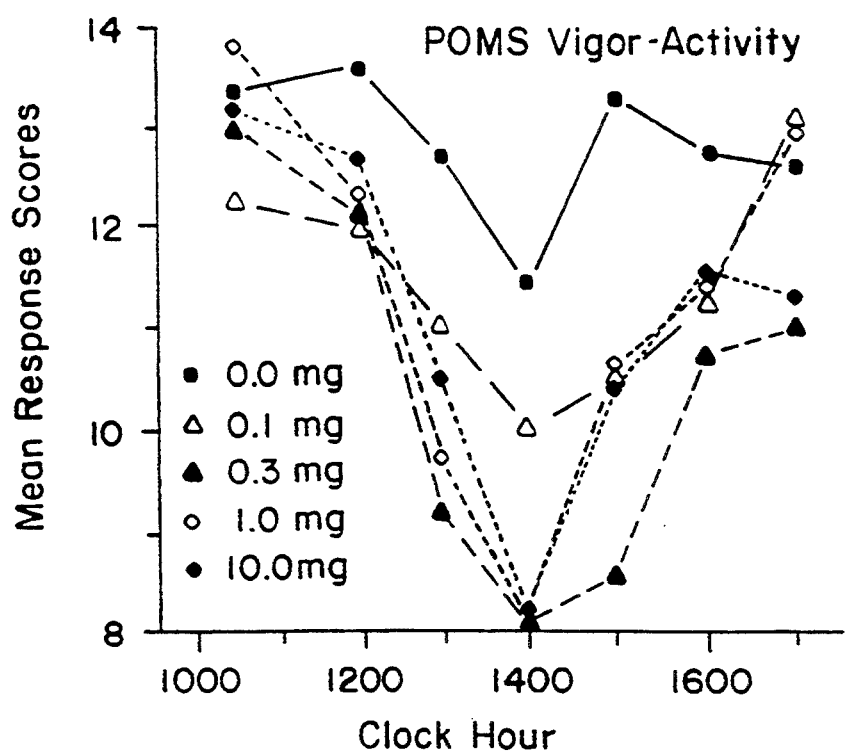
Figure 10C:
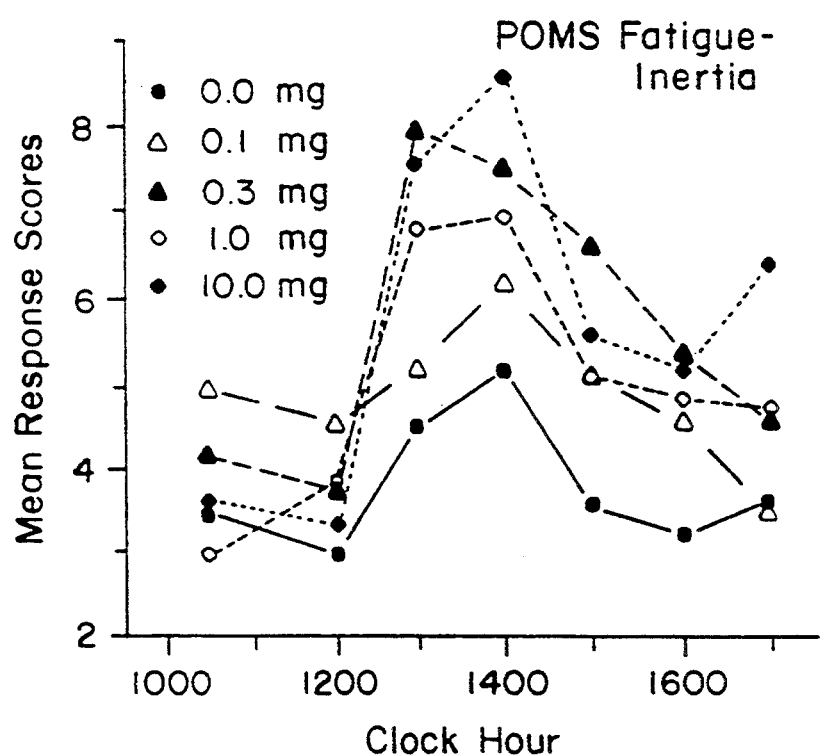
Figure 11:
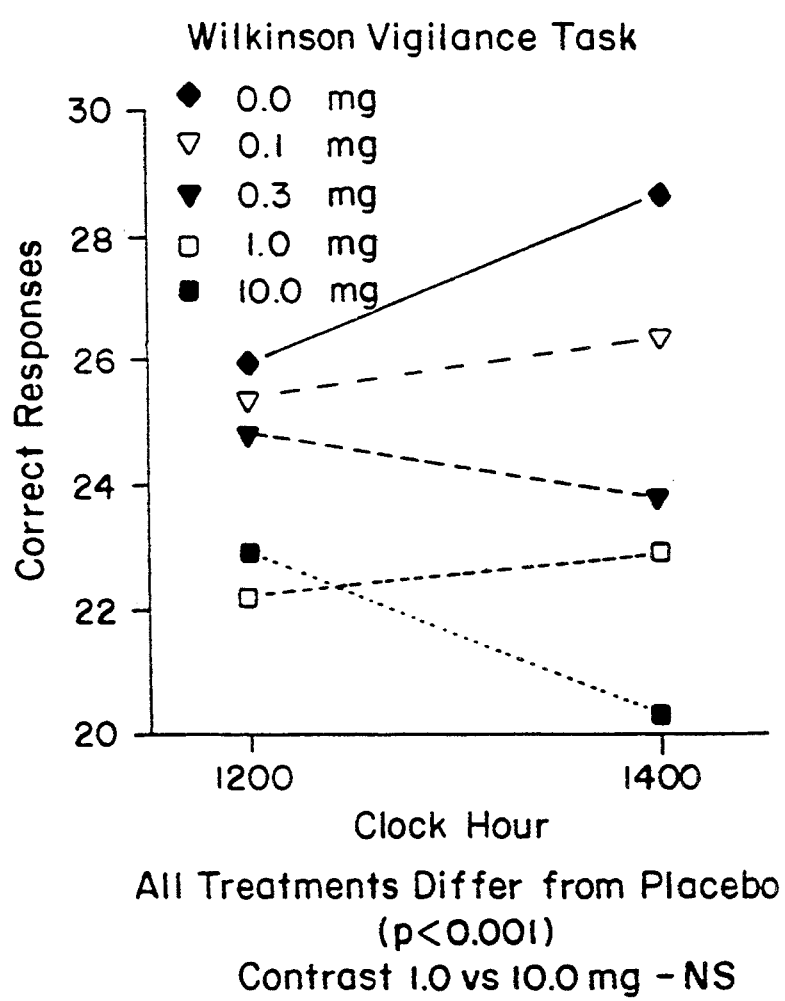
FIG. 11 depicts mean number of correct responses on the Wilkinson Auditory Vigilance Task after ingesting 0.1-10 mg of melatonin or placebo (N=20).

Significant melatonin treatment effects were found for: oral temperature [$F(4,60)=7.90$, $p<0,001$]; sleep test sleep onset latency [$F(4,60)=6.65$, $p<0,001$] (FIG. 9A); sleep duration [$F(4,60)=7.80$, $p<0.001$] (FIG. 9B), self-reported sleep onset latency [$F(4,60)=10.52$, $p<0,001$] (FIG. 9C), and post-sleep-test Stanford Sleepiness Scale (SSS) responses [$F(4,60)=3.11$, $p<0/05$] (FIG. 9D). SSS responses [$F(4,60)=2.79$, $p<0.05$] (FIG. 10A); POMS Vigor-Activity [$F(4,60)=4.16$, $p<0.01$] (FIG. 10B) and Fatigue-Inertia [$F(4,60)=3.05, p<0.05$] (FIG. 10C) responses were also found to be significant, as were the number of correct responses on the Wilkinson Vigilance task [$F(4,60)=3.42$, $p<0.05$] (FIG. 11) and Four Choice RT response latency [$F(4,60)=3.84$, $p<0.01$].

Table 1 summarizes the planned comparison results. The treatment by order interaction effects were non-significant for all measures except the Stanford Sleepiness Scale [$F(4,60)=4,068$, $p<0,001$]. There were no significant differences among the baseline (1000 h) oral temperature, SSS, or POMS measures. An order effect was found among the Four Choice RT response latency baseline measures [$F(4,60)=15.13$, $p<0.001$], but the treatment and treatment by order interaction effects were non-significant.

TABLE 1

Mean Differences+ of Planned Comparisons following Significant Overall F Tests

|  | 0.0 vs. 0.1, 0.3, 1.0 & 10 | 0.1 vs 0.3, 1.0 & 10 | 0.3 vs. 1.0 & 10 | 1.0 vs. 10 |
|---|---|---|---|---|
| Oral Temperature | −0.21** | −0.18** | −0.14** | −0.13 |
| Stanford Sleepiness Scale | 0.42** | 0.25** | −0.05** | −0.01 |
| Profile of Mood States: | | | | |
| Vigor-Activity Scale | −2.02** | −0.77** | 0.84** | −0.05 |
| Fatigue-Inertia Scale | 1.75** | 0.97** | −0.22** | 0.72 |
| Sleep Test: | | | | |
| Sleep Onset Latency | −9.46** | −2.67** | −1.64** | 0.70 |

TABLE 1-continued

Mean Differences+ of Planned Comparisons following Significant Overall F Tests

| | 0.0 vs. 0.1, 0.3, 1.0 & 10 | 0.1 vs 0.3, 1.0 & 10 | 0.3 vs. 1.0 & 10 | 1.0 vs. 10 |
|---|---|---|---|---|
| Sleep Duration | 10.20** | 2.67** | 1.24** | −1.62 |
| Self Reported Sleep Latency | −10.53** | −3.91** | −1.36** | 2.62 |
| SSS Responses | 0.61** | 0.48** | 0.05** | −0.40 |
| Wilkinson Auditory Vigilance: # Correct Responses | −3.72* | −3.03 | −2.19* | −0.92* |
| Four Choice RT: Correct Response Latency | 10.06** | 13.25 | 7.57* | 2.62* |

+Values in table are an average of the subsequent melatonin doses (mg) minus the first dose listed in the heading. All comparisons were made with 5 and 15 degrees of freedom, N = 20 (see text for details of missing value substitutions)
* = p < 0.05, ** = p < 0.001.

Table 2 contains the mean (SEM) oral temperature and response levels following ingestion of 0.1, 0.3, 1.0 and 10.0 mg of melatonin or placebo.

TABLE 2

Mean (SEM) Measured Responses

| | Melatonin Ingested (mg) | | | | |
|---|---|---|---|---|---|
| | 0.0 | 0.1 | 0.3 | 1.0 | 10.0 |
| Oral Temperature (°F.) | 97.55 (0.06) | 97.47 (0.06) | 97.39 (0.05) | 97.31 (0.05) | 97.18 (0.05) |
| Stanford Sleepiness Scale | 3.15 (0.10) | 3.38 (0.10) | 3.66 (0.10) | 3.62 (0.12) | 3.61 (0.13) |
| Profile of Mood States: | | | | | |
| Vigor-Activity Scale | 12.73 (0.59) | 11.29 (0.64) | 9.96 (0.57) | 10.83 (0.65) | 10.78 (0.63) |
| Fatigue-Inertia Scale | 3.83 (0.40) | 4.85 (0.42) | 5.97 (0.44) | 5.39 (0.49) | 6.11 (0.53) |
| Sleep Test: | | | | | |
| Sleep Onset Latency (min) | 17.06 (2.43) | 9.61 (1.84) | 8.03 (1.60) | 6.04 (1.65) | 6.74 (1.24) |
| Sleep Duration (min) | 11.36 (2.34) | 19.56 (1.79) | 21.40 (1.63) | 23.45 (1.67) | 21.83 (1.41) |
| Self Reported Sleep Latency (min) | 20.55 (2.23) | 12.95 (@2.07) | 9.95 (1.69) | 7.28 (1.33) | 9.90 (2.07) |
| SSS Responses | 3.80 (0.22) | 4.05 (0.26) | 4.50 (0.22) | 4.75 (0.25) | 4.35 (0.26) |
| Wilkinson Auditory Vigilance # Correct Responses | 27.30 (1.48) | 25.85 (1.32) | 24.28 (1.53) | 22.55 (1.66) | 21.63 (1.56) |
| Four Choice RT Correct Response Latency (ms) | 359.41 (8.25) | 359.54 (7.36) | 367.74 (7.65) | 374.00 (9.08) | 376.62 (9.86) |

As Table 2 indicates, response levels for some measures did not consistently increase or decrease relative to dose of melatonin ingested. For instance, self-reported SSS responses were greatest and POMS Vigor-Activity scale responses were smallest after ingesting 0.3 mg of melatonin. Pairwise comparisons were calculated to aid in interpretation of these data. Mean oral temperature measures were significantly less, relative to placebo, after ingesting 1.0 and 10 mg of melatonin Δ−0.24 and −0.37° F. respectively). Oral temperatures measured after ingesting 1.0(Δ−0.16) and 10 (Δ−0.29) mg of melatonin were also less than those measured after ingesting 0.1 mg of melatonin. After ingestion of 10 mg of melatonin, oral temperature also decreased relative to the 0.3 and 1.0 doses (Δ−0.21 and −0.13, respectively). SSS responses indicated greater feelings of sleepiness, relative to placebo, after ingesting 0.3, 1.0 and 10 mg of melatonin (Δ+0.51, +0.47, and +0.46 respectively). POMS responses indicated a decrease in self-reported feelings of Vigor-Activity, relative to placebo, after ingesting 0.3, 1.0, and 10 mg of melatonin (Δ−2.77, −1.90, and −1.95 respectively). Feelings of Vigor-Activity were also decreased after ingesting 0.3 mg relative to 0.1 mg of melatonin (Δ−1.33). POMS responses indicated an increase in self-reported feelings of Fatigue-Inertia, relative to placebo, after ingesting 0.3, 1.0, and 10 mg of melatonin (Δ+2.14, +1.56, and +2.28 respectively).

Sleep test sleep onset latencies were shorter, relative to placebo, after ingesting 0.1, 0.3, 1.0 and 10 mg of melatonin (Δ−7.45, −9.03, −11.02, and −10.32, minute, respectively). The duration of sleep (i.e., switch release) experienced during the sleep test was greater, relative to placebo, for the 0.1, 0.3, 1.0, and 10 mg melatonin doses (Δ 8.20, 10.04, 12.09, and 10.47 minute, respectively). Sleep test self-reported sleep-latencies were shorter, relative to placebo, for the 0.1, 0.3, 1.0, and 10 mg melatonin doses (Δ−7.60, −10.60, −13.27, and −10.65 minutes, respectively). Subjects also indicated that they slept more quickly after ingesting 1.0 mg, relative to 0.1 mg of melatonin (Δ−5.67). Responses to the post sleep test SSS indicate that subjects felt sleepier after ingesting 1.0 and 10 mg of melatonin than when ingesting placebo (Δ+0.70 and +0.95 respectively). Post sleep test SSS responses also indicate that 1.0 mg of melatonin caused greater feelings of sleepiness than 0.1 mg (Δ+0.70). Fewer Wilkinson Auditory Vigilance task correct responses were recorded, relative to placebo, after subjects ingested 1.0 and 10 mg of melatonin (Δ−4.75 and −5.67 respectively). Correct Four Choice RT response latencies were greater (i.e., longer) after ingesting 10 mg, relative to placebo and 0.1 mg of melatonin (Δ+17.21 and 14.46 ms respectively). All of the pairwise comparison results reported above were significant at the p<0.05 level.

Significant order effects were found on the Wilkinson Auditory Vigilance, Simple RT, Four Choice RT, and Symbol Digit Substitution tasks. These results indicate that subjects tended to respond more accurately (Symbol Digit Substitution responses and RT response latencies) with practice or less frequently (Wilkinson Auditory Vigilance) on subsequent test days. These changes are of little interest because significant treatment by order interactions were not found on these measures the Latin Square is balanced to compensate for order effects and similar results have been previously reported.

There were consistent patterns of variance over time among the mood scale measures. Subjects' SSS [F(5,75)=17.50, p<0,001] and POMS Fatigue-Inertia [F(5,75)=8.04, p<0,001] responses indicate that they felt sleepiest and most fatigued and that they felt the least vigorous (POMS Vigor-Activity scale [F(5,75)=12.79, p<0,001]) at 1400 h (see FIG. 10A-10C). Oral temperatures were consistently low at 1200 and 1400 h (means were 96.85° and 97.09° F., respectively). Mean Four Choice RT response latencies were the greatest at 1300 h (i.e., 377.77 ms) and decreased to 360.15 ms at 1700 h. Significant treatment by time interactions were found in oral temperature [F(24,360)=1.601, p<0.05] and number of correct responses on the Four Choice RT task [F(12,180)=1.92, p<0.03].

Thus, as a result of the work presented herein, a single dose of melatonin can now be used as a clinically effective sleep-inducing aid. Administration of a melatonin dose, in particular, a dose of 0.1–0.3 mg during the daytime, which raises serum melatonin concentrations to within the normal nocturnal range, or of slightly higher doses (1.0–10 mg), have been shown to cause hypnotic effects, relative to placebo. These effects include a decrease in objective and self-estimated sleep onset latency, an increase in sleep duration and sleepiness following waking. Self-reported feelings of vigor decreased.

Surprisingly, as described herein, even a single physiological dose of melatonin, between 0.1 and 1 mg, and, in particular 0.1 and 0.3 mg, is effective to induce sleep in subjects tested, as measured by the performance tests described in Example 3. Previous beliefs that, because of its short biological half-life, only very high doses (i.e., pharmacologic doses) of melatonin, or smaller doses chronically administered, or administration by other than an oral route would be necessary for melatonin to be an effective inducer of sleep, have now been dispelled.

Therefore, as a result of these studies, it has been determined that the amount of exogenous melatonin administered, in an acute dose, effective to induce sleep in humans, is between 0.1–1.0 mg, and in particular, is 0.1 or 0.3 mg. A dose of exogenous melatonin effective to induce sleep in an individual need only acutely raise blood levels of melatonin to normal nocturnal levels. These results suggest that the physiologic secretion of endogenous melatonin may be an important and direct-acting factor causing sleep onset.

The invention is further illustrated by the following examples, which are not intended to be limiting in any way.

EXAMPLE 1

Patient Selection and Protocol for Study I

Twenty healthy male subjects (Mean Age=25±1.47 SEM, Range, 19–30 years) participated in this study. Prior to admission to the study, each subject signed an informed consent form, had a physical examination to ensure that he was in good health, and completed two 1.5 hour training sessions to familiarize him with testing procedures and the performance test battery. Subjects were also screened for depressive symptoms using the Hamilton Psychiatric Rating Scale for Depression (Hamilton, M., Br. *J. Soc. Clin. Psychol.*, 6:278–296 (1967)) with a special addendum for Seasonal Affective Disorder (Rosenthal, N. E., et al., *THE PSYCHOBIOLOGY OF BULIMIA*, eds. Hudson, II and Pope, J. G. Jr., American Psychiatric Press, Wash. D.C., pp. 205–228 (1987)). The protocol was approved by the MIT Clinical Research Center Advisory Board and Committee on the Use of Humans Experimental Subjects. All subjects were paid for their participation in the experiment.

The study was double-blind and placebo-controlled. A repeated measures, within subjects 5×5 Latin Square design was employed. The subjects participated in five 7.5 hours (0930–1700 h) testing sessions. At least five days elapsed between successive test sessions. Capsules containing 10, 20, 40, or 80 mg of melatonin or placebo were administered (p.o.) at 1145 h of each test day. Treatment order was determined by a balanced Latin Square design.

On admission, a catheter with a heparin lock was implanted in a forearm vein for blood sample withdrawal. Blood samples were taken from each volunteer at 1000, 1200, 1300, 1400, 1500, 1600, and 1630 h). Serum samples were separated by centrifugation and stored at −20° C. until they could be assayed for melatonin concentration. Oral temperature, blood pressure, heart rate, and sleepiness were assessed hourly. Digital oral thermometers were used to measure temperature (Model No. 403001, Becton Dickinson Consumer Products).

Subjects were required to sit at an assigned computer workstation, with eyes open, and to complete interactive computer tasks throughout the day. A standard lunch was served between 1100 and 1130 h and toilet breaks (<5 min) were allowed. The task order and time of testing were held constant across test days (see Table 3 for detailed schedule).

TABLE 3

| Time | Activity | Time | Activity |
|---|---|---|---|
| 0930 | Subject Arrives | 1400 | Blood Sample #4 |
| | Insert Catheter | | Stanford Sleepiness |
| | Blood Sample #1 | | Scale |
| 1030 | Baseline Testing | | Wilkinson Auditory |
| | Profile of Mood States | | Vigilance |
| | Digit Symbol Substitution | 1500 | Blood Sample #5 |
| | Stanford Sleepiness Scale | | Profile of Mood States |
| | Simple Auditory RT | | Digit Symbol |
| | Four Choice RT | | Substitution |
| 1100 | Eat Lunch | | Stanford Sleepiness |
| 1145 | Take Melatonin Capsules | | Scale |
| 1200 | Blood Sample #2 | | Simple Auditory RT |
| | Stanford Sleepiness Scale | | Dual Task |
| | Wilkinson Auditory | | Four Choice RT |
| | Vigilance | 1600 | Blood Sample #6 |
| 1300 | Blood Sample #3 | | Profile of Mood |
| | Profile of Mood States | | States |
| | Digit Symbol Substitution | | Digit Symbol |
| | Stanford Sleepiness Scale | | Substitution |
| | Simple Auditory RT | | Stanford Sleepiness |
| | Dual Task | | Scale |
| | Four Choice RT | | Simple Auditory RT |
| | | | Four Choice RT |
| | | 1630 | Blood Sample #7 |
| | | | Remove Catheter |
| | | | Release Subject |

| Task Name | Approximate Duration (min.) | Number of Repetitions |
|---|---|---|
| Profile of Mood States | 5 | 4 |
| Digit Symbol Substitution | 2 | 4 |
| Stanford Sleepiness Scale | 1 | 6 |
| Simple Auditory Reaction Time | 5 | 4 |
| Dual Task | 30 | 2 |
| Four Choice Reaction Time | 5 | 4 |
| Wilkinson Auditory Vigilance Task | 60 | 2 |

A repeated measures within-subjects 5×5 Latin Square analysis was used for all measures. The data for one subjects' fifth test session were lost due to experimenter error and group means were substituted to maintain the integrity of the Latin Square for analysis purposes. Only after-treatment measures were analyzed. Pre-treatment measures are shown in the figures to illustrate baseline uniformity. The following planned contrasts were used to examine individual dose effects: 1) placebo versus 10, 20, 40, and 80 mg of melatonin; 2) 10 versus 20, 40, and 80 mg of melatonin; 3) 20 versus 40 and 80 mg of melatonin and; 4) 40 versus 80 mg of melatonin. Only treatment effects for which there are significant contrasts were reported.

EXAMPLE 2

Melatonin Assay

Melatonin concentrations were measured in duplicate on 1 ml serum samples by radioimmunoassay (RIA) using CIDtech Ultraspecific Melatonin Antiserum (CID-tech Research Inc., Hamilton, Ontario; Brown, et al. 1983). The assay procedure is described in detail in Brzenzinski, A., et al., *J. Clin. Endocriol. Metab.*

64:865–867 (1987). Briefly, the melatonin in 1 ml samples of serum were extracted into 5 ml of chloroform; the organic extracts were evaporated to dryness under a stream of nitrogen; and the residues were then redissolved in phosphate buffer. Samples of the buffered serum extracts were then analyzed by RIA. The interassay coefficient of variation was 9.1% for a mean serum concentration of 102 pg/ml. The sensitivity of the assay (defined as three times the standard deviation of maximum binding) in the present study was 8 pg/ml.

EXAMPLE 3

Performance Test Battery

All performance tasks were administered on AT-class microcomputers equipped with hard drives and color VGA monitors. The computers were modified to port the speaker output to an audio amplifier (Realistic Model: SA-150) equipped with stereo headphones (Realistic Model: NOVA '40). To reduce the possibility of experimenter-induced bias, all tasks and instructions were automated by using a sequence of computer menus.

Dual Task

In this test, the subjects must simultaneously perform two tasks, a modified version of the Bakan vigilance test (Jones, D. M., et al., *J. Appl. Psych.*, 64:627–634 (1979)) and the "estimation of two classes of events in a signal stream" (PROP) test (Smith, A. P., et al., *Neuropsychobiology*, 18:144–148 (1987)). The Bakan vigilance task presents, on the CRT screen, a sequence of three-digit numbers every 1.5 seconds for 30 minutes. Each successive number usually differs from the previous number by one digit. However, occasionally all three digits are repeated. The subjects' task is to detect the occurrence of these repeated sequences and to respond by pressing a key on the computer keyboard. Six blocks of 200 trials are presented during each test. Twenty-two three digit number sequences are repeated during each block of trials. A single digit or letter is presented to the right of and simultaneously with the three digit number of the Bakan series. At the end of each block of trials, the subjects are required to estimate the proportion of letters (versus numbers) occurring in the last block of PROP stimuli. Subjects respond by moving a cursor on the computer screen to select a choice. The actual proportion varies randomly between 0.2 and 0.8, in increments of 0.1, for each block of 200 stimuli. The number of true positive and true negative responses, as well as the proportions estimated, and those actually presented throughout each block of trials, are retained in a computer file.

Wilkinson Auditory Vigilance Task

The Wilkinson Auditory Vigilance Task is a computer adaptation of the task described by R. T. Wilkinson *PROGRESS IN CLINICAL PSYCHOLOGY*, Reiss, B. F. and Abt, L. A. (eds) Grune & Stratton, N.Y. pp. 28–43 (1969), with several modifications. Throughout the task, subjects must listen to a series of 500 Hz 70 db (SPL) tones, presented at a rate of one tone every two seconds. The tones are of two lengths, long (500 msec) and short (variable msec). The subjects' task is to press a key when the short tone is heard. The current version of the task was similar to Wilkinson's original version in that the tones were presented for one hour (1,800 tones) and 40 (2.2%) of the tones were short. Because the subjects were tested in a quiet room using headphones, no masking noise was used.

In addition, the difficulty of short tone detecting was evaluated and adjusted individually for each subject during training, so each subject detected a short tone approximately 50% of the time (Lieberman, H. R., et al., *Am. J. Clin. Nutr.*, 44:772–778 (1985)). The length of the short tones ranged from 350 to 450 msec (Mean & Mode=400 msec). Investigators monitored the subjects throughout administration of this task to ensure that they did not sleep or close their eyes. The numbers of true positive, true negative, and premature responses were retained in a data file.

Four Choice Reaction Time (RT)

This test resembles the Wilkinson Four Choice RT task and is a measure of visual vigilance (Wilkinson, A. T. and Houghton, D., *Behav. Res. Meth. Instrum.* 7:441–446 (1975)). Subjects are presented with a series of visual stimuli at one of four adjacent spatial locations on a CRT screen. The subject must correctly indicate the correct location of each stimulus by striking one of four corresponding adjacent keys on a microcomputer keyboard. Four hundred trials were administered. The mean response latency and variance, as well as the number of true positive and true negative responses are registered and retained. The numbers of premature responses (responses made during the 400 msec pause between stimuli) and time-out errors (failure to respond within 2000 msec of stimulus presentation) are also retained. Five warm-up stimuli and the response errors are not included in the total number of trials presented.

Simple Auditory Reaction Time

In this task, the subject responds, as rapidly as possible, to the onset of an auditory signal. The test trials are presented in rapid succession following five warm-up trials. A 300 msec 360 Hz tone warns the subject that a trial is about to begin. After a random delay of 100 to 900 msec, a 1000 Hz tone signals the subject to respond. Subjects are instructed to respond as quickly as possible after the onset of the 1000 Hz tone. The subjects' response latency appears on the computer screen for 300 msec between each trial. A warning message accompanied by an oscillating error tone occurs if the subject responds prematurely (prior to or within 50 msec of the onset of the stimulus tone) or fails to respond within 2000 msec. The subject acknowledges premature and time-out errors by pressing the Enter key. A 1000 msec delay occurs between error acknowledgment and the next trial to allow time for the subject to reposition his hand. The response latency and variance, as well as the number of premature and time-out errors are retained in a data file. The task continues until 200 reaction times have been recorded.

Digit-Symbol Substitution Task

This task is a microcomputer implementation of the Digit-Symbol Substitution Task of the WAIS-R Intelligence scale (File, S. E., et al., *J. Clin. Psychopharmacol.*, 2:102–106 (1982)). The task consists of a display of nine symbols in a row of boxes at the top of the screen, a display of nine corresponding numbers (i.e., 1 through 9) in a row of boxes below the symbols, a "cue" box and an "answer" box. The subject must use the numerical keypad to enter the number corresponding to the symbol that appears in the "cue" box, using the symbols and numbers at the top of the screen as a guide. The task is timed and the subject is instructed to enter as many answers as possible within 90 seconds. The first five symbols presented are considered practice trials and are not included in the final output or in the timed portion of the test. The symbol associated with a given digit does not change within a 90 second set of trials, but does change (randomly) each time the task is activated to prevent subjects from memorizing response keys. No response feedback is given to the subject, but a warning tone occurs if the subject presses a non-numerical key on the keyboard.

Mood and Sleepiness Measures

The Profile of Mood States (POMS; McNair, P. M., et al., PROFILE OF MOOD STATES MANUAL, Educational and Industrial Testing Service, San Diego, Calif., (1971) and Stanford Sleepiness Scale (SSS; Hoddes, E., et al., Psychophysiology, 10:431–436 (1973) were adapted to computer administration so the subjects could indicate choices by moving a cursor instead of using a pencil and paper. The SSS is a self-rated, 7-point scale designed to quantify the progressive stages of the sleep-alertness continuum. The POMS is a self-report scale that consists of 65 adjectives, each of which is rated on a 5-point scale. Factor analysis yields the following factors: Tension-Anxiety, Depression-Dejection, Anger-Hostility, Vigor-Activity, Fatigue-Inertia, and Confusion-Bewilderment.

EXAMPLE 4

Patient Selection and Protocol for Study II

Three healthy male subjects participated in the study. Prior to admission to the study, each subject signed an informed consent form, had a physical examination to ensure that he was in good health, and completed two 1.5 hour training sessions to familiarize him with testing procedures and the performance test battery. Subjects were also screened for depressive symptoms using the Hamilton Psychiatric Rating Scale for Depression (Hamilton, M., Br. J. Soc. Clin. Psychol., 6:278–296 (1967) with a special addendum for Seasonal Affective Disorder (Rosenthal, N. E., et al., THE PSYCHOBIOLOGY OF BULIMIA, eds. Hudson, II and Pope, J. G. Jr., American Psychiatric Press, Wash. D.C., pp. 205–228 (1987)). The protocol was approved by the MIT Clinical Research Center Advisory Board and Committee on the Use of Humans as Experimental Subjects. All subjects were paid for their participation in the experiment.

The study was double-blind and placebo-controlled. A repeated measures, within subjects, 5×5 Latin Square design, with only three rows of the square occupied, was employed. The subjects participated in five 8.5 hour (0930–1800 h) testing sessions. At least five days elapsed between successive test sessions. Capsules containing 0.1, 0.3, 1.0 or 10.0 mg of melatonin or placebo were administered (p.o.) at 1145 h of each test day. Treatment order was determined by a Latin Square design.

Subjects were asked to abstain from alcohol, nicotine, and caffeine consumption for 24 hours prior to testing, and to consume a standard, caffeine-free breakfast on the day of the test. Subjects were instructed to maintain their normal daily sleep/activity cycles during the study, particularly the day before a test session. Testing was not conducted on Mondays or following three-day weekends (since sleep patterns are often disrupted during such periods).

On admission, a catheter with a heparin lock was implanted in a forearm vein for blood sample withdrawal. Blood samples were taken from each volunteer at 1000, 1200, 1300, 1400, 1500, 1600, 1700 and 1800 h. Serum samples were separated by centrifugation and stored at 20° C. until they could be assayed for melatonin concentration. Oral temperature, blood pressure, heart rate, and sleepiness were assessed hourly. Digital oral thermometers were used to measure temperature (Model No. 403001, Becton Dickinson Consumer Products).

Subjects were required to sit at an assigned computer workstation, with eyes open, and to complete interactive computer tasks throughout the day. A standard lunch was served between 1100 and 1130 h and toilet breaks (less than 5 min) were allowed. The task order and time of testing were held constant across test days (see Table 4 for detailed schedule).

Because only three subjects were tested in this study, there were insufficient data for inferential analysis. However, the study was based on inspection of the descriptive statistics included herein. A repeated measures, within-subjects, 5×5 Latin Square analysis can be used for all measures. Only after-treatment measures are analyzed. The following planned contrasts can be used to examine individual dose effects: 1) placebo versus 0.1, 0.3, 1.0 and 10.0 mg of melatonin; 2) 10.0 versus 0.1, 0.3 and 1.0 mg of melatonin; 3) 0.1 versus 0.3 and 1.0 mg of melatonin and; 4) 0.3 versus 1.0 mg of melatonin.

TABLE 4

| Time Line of Testing | | | |
|---|---|---|---|
| 0930 | Subject Arrives Insert Catheter Blood Sample #1 | 1400 | Blood Sample #4 Stanford Sleepiness Scale |
| 1030 | Baseline Testing Profile of Mood States Digit Symbol Substitution Stanford Sleepiness Scale Simple Auditory RT Four Choice RT | 1500 | Wilkinson Auditory Vigilance Blood Sample #5 Profile of Mood States Digit Symbol Substitution |
| 1100 | Eat Lunch | | Stanford Sleepiness Scale |
| 1145 | Take Melatonin Capsules | | Simple Auditory RT |
| 1200 | Blood Sample #2 Stanford Sleepiness Scale Wilkinson Auditory Vigilance | | Dual Task Four Choice RT |
| | | 1600 | Blood Sample #6 Profile of Mood States |
| 1300 | Blood Sample #3 Profile of Mood States Digit Symbol Substitution Stanford Sleepiness Scale Simple Auditory RT Dual Task Four Choice RT | | Digit Symbol Substitution Stanford Sleepiness Scale Simple Auditory RT Four Choice RT |
| | | 1700 | Blood Sample #7 Profile of Mood States Digit Symbol Substitution Stanford Sleepiness Scale Simple Auditory RT Four Choice RT |
| | | 1800 | Blood Sample #8 Remove Catheter Release Subject |

| Task Name | Approximate Duration (min.) | Number of Repetitions |
|---|---|---|
| Profile of Mood States | 5 | 5 |
| Digit Symbol Substitution | 2 | 5 |
| Stanford Sleepiness Scale | 1 | 7 |
| Simple Auditory Reaction Time | 5 | 5 |
| Dual Task | 30 | 2 |
| Four Choice Reaction Time | 5 | 5 |

| TABLE 4-continued | | |
|---|---|---|
| Wilkinson Auditory Vigilance Task | 60 | 2 |

EXAMPLE 5

PATIENT SELECTION AND PROTOCOL FOR STUDY III

Twenty healthy male volunteers (Mean Age=23.05±4.22 SEM, Range 18–24 years) participated in this study. Prior to admission to the study, each subject gave his informed consent, had a physical examination to ensure he was in good health, and completed two 1.5 hour training sessions to familiarize him with testing procedures and the performance test battery. Subjects were also screened for depressive symptoms using the Hamilton Psychiatric Rating Scale for Depression (Hamilton, 1967) with a special addendum for Seasonal Affective Disorder (Rosenthal et al. 1987). All subjects were paid for their participation in the experiment.

The study was double-blind and placebo-controlled. A repeated measures, within subjects, 5×5 Latin Square design was employed. The subjects participated in five eight-hour (0930–1730 h) testing sessions. At least five days elapsed between successive test sessions. Capsules containing 0.1, 0.3, 1.0 or 10 mg of melatonin or placebo were administered (p.o) at 1145 h each test day. Treatment order was determined by the balanced Latin Square design.

Oral temperatures were monitored hourly. Blood was sampled via an indwelling venous catheter, at regular intervals, for subsequent serum melatonin measurement by radioimmunoassay. Serum samples were separated by centrifugation and stored at −20° C. until submitted to melatonin assay as described in Example 2.

Throughout test sessions, subjects were required to sit at an assigned computer workstation with eyes open. The task order and time of testing were held constant across test days. All instructions, performance tasks and mood questionnaires were automated to reduce the possibility of experimenter-induced bias. The performance tasks used were coded in-house and include measures of: 1) Auditory Vigilance; 2) Four Choice Reaction Time; 3) Simple Reaction Time; and 4) Symbol Digit (Modalities) Substitution. Mood questionnaires included the Profile of Mood States (POMS) and Stanford Sleepiness Scale (SSS). Details of the tasks and their administration are as described in Example 3. The mood questionnaires were completed at 1030 h and at hourly intervals beginning at 1200 h. The Simple and Four Choice RT and Symbol Digit Substitution tasks were completed at 1030, 1300, 1500, 1600, and 1700. The auditory Vigilance task was administered at 1200 and 1400 h. Subjects were allowed to leave the workstations during lunch (a standard lunch was served between 1100 and 1130 h), toilet breaks (<5 min), and during the sleep test.

Subjects participated in a sleep test between 1330 and 1400. They were asked to recline (on either a bed or reclining chair) and relax with eyes closed, in a quiet, darkened room. They held a 1" plastic tube, which bore a positive pressure switch, in each hand. They were asked to rest their hands, palm up, along side their body, and to depress the switch with the last segment of their index fingers. Release of the switch on either tube was recorded as a pen deflection on an event-recorder. An investigator remained in attendance with the subjects to ensure that they followed instructions. An event-timer relay was randomly activated to reduce the possibility that release of a positive pressure switch (which made a soft clicking sound) would be identified as a significant event by the subjects. After 30 minutes, the subjects were asked to stop relaxing and/or awakened. They were then asked: 1) if they fell asleep; 2) if so, how long did it take to fall asleep; and 3) to respond to the Stanford Sleepiness Scale. A self-reported sleep latency of 30 min was recorded for subjects indicating that they had not fallen asleep. Latency to switch release was measured from the beginning of instruction presentation, to the first full minute of switch release. Total switch time release was measured as the total length of time a recording pen was deflected (the smallest interval of pen deflection measured was 1 minute, accuracy=0.25 min). (One subject failed to release a switch during a sleep test session, but was identified as sleeping by his continued snoring. Sleep onset for this subject was recorded as occurring after two minutes of continued snoring. The subject reported that he had fallen asleep when questioned later.)

The after-treatment dependent measures were each assessed using a repeated measures, within subjects, 5×5 Latin Square analysis. Orthogonal planned comparisons were used to evaluate differences among the melatonin/placebo treatment conditions if a significant ($p<0.05$) treatment effect was found. The comparisons chosen were: 1) placebo versus all melatonin treatments; 2) 0.1 versus 0.3, 1.0, and 10 mg of melatonin; 3) 0.3 versus 1.0 and 10 mg of melatonin; and 4) 1.0 versus 10 mg of melatonin. Pairwise comparisons were subsequently calculated for these measures (repeated measures t-Tests for the Sleep Test Data and ANOVAs for the other measures) because inspection of the data suggested that the planned contrasts provided an insufficient basis for result interpretation. Only main effects, treatment (i.e., melatonin dose), order (i.e., test day), and time which resulted in significant contrasts, and interaction effects, are reported. There were some missing data due to difficulties with equipment and blood sampling. Group means were substituted for the 1700 h, 0.1 mg, 1300 h 1.0 mg, 1700 h 1.0 mg, and 1000 h 10 mg measures for subjects 15, 03, 16, and 15 respectively, on most performance measures. Blood samples were not drawn during subject 01's placebo testing due to difficulties with catheterization and group means were substituted for this data also. Group means serum melatonin levels were substituted for six other missing data points.

Equivalents

Those skilled in the art will know, or be able to ascertain using no more than routine experimentation, many equivalents to specific embodiments of the invention described herein. These and all other equivalents are intended to be encompassed by the following claims.

I claim:

1. A method of inducing sleep in an individual comprising orally administering to the individual, within about two hours of when sleep is desired, an acute single dose of melatonin, said single dose being less than 1 mg and effective to raise the peak plasma level of melatonin in the individual to within normal physiological nocturnal levels.

2. The method of claim 1 wherein said oral single dose of melatonin is administered at night.

3. The method of claim 1 wherein said oral single dose of melatonin is 0.3 mg.

4. The method of claim 1 wherein said oral single dose of melatonin is 0.1 mg.

5. A method of inducing sleep in an individual comprising orally administering to the individual, when sleep is desired, an acute single dose of melatonin sufficient to result in peak melatonin blood levels of the individual within normal physiological nocturnal melatonin levels, thereby inducing sleep, said single dose being less than 1 mg.

6. The method of claim 5 wherein said single dose of melatonin is 0.3 mg.

7. The method of claim 5 wherein said single dose of melatonin is 0.1 mg.

8. The method of claim 1 which further comprises allowing the individual to fall asleep within about two hours of administration of said single dose.

9. The method of claim 5 which further comprises allowing the individual to fall asleep within about two hours of administration of said single dose.

* * * * *